US012751845B2

(12) United States Patent
Stappenbeck et al.

(10) Patent No.: US 12,751,845 B2
(45) Date of Patent: Oct. 6, 2026

(54) LOADING TOOL AND METHOD FOR LOADING A PROSTHESIS

(71) Applicant: TRICARES SAS, Paris (FR)

(72) Inventors: Nadine Stappenbeck, Aschheim (DE); Helmut Straubinger, Aschheim (DE)

(73) Assignee: TRICARES SAS, Paris (FR)

( * ) Notice: Subject to any disclaimer, the term of this patent is extended or adjusted under 35 U.S.C. 154(b) by 601 days.

(21) Appl. No.: 17/277,496

(22) PCT Filed: Sep. 19, 2019

(86) PCT No.: PCT/EP2019/075216
§ 371 (c)(1),
(2) Date: Mar. 18, 2021

(87) PCT Pub. No.: WO2020/058427
PCT Pub. Date: Mar. 26, 2020

(65) Prior Publication Data

US 2022/0039980 A1 Feb. 10, 2022

(30) Foreign Application Priority Data

Sep. 21, 2018 (EP) .................................... 18196047

(51) Int. Cl.
*A61F 2/95* (2013.01)
*A61F 2/24* (2006.01)
*A61F 2/966* (2013.01)

(52) U.S. Cl.
CPC .......... *A61F 2/9525* (2020.05); *A61F 2/2436* (2013.01); *A61F 2/966* (2013.01)

(58) Field of Classification Search
CPC ...... A61F 2/9525; A61F 2/2436; A61F 2/966; A61F 2/95; A61F 2/9522
See application file for complete search history.

(56) References Cited

U.S. PATENT DOCUMENTS

| | | | |
|---|---|---|---|
| 6,669,724 | B2 | 12/2003 | Park et al. |
| 8,070,800 | B2 | 12/2011 | Lock et al. |
| 8,628,571 | B1 | 1/2014 | Hacohen et al. |
| 9,066,801 | B2 | 6/2015 | Kovalsky et al. |
| 10,039,639 | B2 | 8/2018 | Marchand et al. |
| 10,245,143 | B2 | 4/2019 | Gross et al. |
| 10,543,077 | B2 | 1/2020 | Tuval et al. |
| 10,702,378 | B2 | 7/2020 | Miyashiro |

(Continued)

FOREIGN PATENT DOCUMENTS

| | | | |
|---|---|---|---|
| EP | 3202371 | A1 | 8/2017 |
| WO | WO-2010/008548 | A2 | 1/2010 |

(Continued)

OTHER PUBLICATIONS

International Search Report and Written Opinion for International Application No. PCT/EP2019/053633, mailed May 3, 2019 (12 pages).

(Continued)

*Primary Examiner* — Thomas C Barrett
*Assistant Examiner* — Mikail A Mannan
(74) *Attorney, Agent, or Firm* — The Dobrusin Law Firm, P.C.

(57) ABSTRACT

The present invention relates to a heart valve prosthesis loading device and a method for loading a heart valve prosthesis onto a delivery system.

12 Claims, 28 Drawing Sheets

A

B

(56) References Cited

U.S. PATENT DOCUMENTS

| | | | | |
|---|---|---|---|---|
| 10,945,839 | B2 | 3/2021 | Alon et al. | |
| 10,952,851 | B2 | 3/2021 | Marchand | |
| 11,109,965 | B2 | 9/2021 | Iyer et al. | |
| 2003/0004537 | A1* | 1/2003 | Boyle | 606/200 |
| 2003/0144725 | A1 | 7/2003 | Lombardi | |
| 2004/0093060 | A1 | 5/2004 | Seguin et al. | |
| 2008/0275540 | A1 | 11/2008 | Wen | |
| 2009/0088836 | A1 | 4/2009 | Bishop et al. | |
| 2009/0138079 | A1 | 5/2009 | Tuval et al. | |
| 2009/0240320 | A1 | 9/2009 | Tuval et al. | |
| 2010/0100167 | A1* | 4/2010 | Bortlein | A61F 2/95 623/1.11 |
| 2011/0137397 | A1 | 6/2011 | Chau et al. | |
| 2011/0245911 | A1 | 10/2011 | Quill et al. | |
| 2011/0264207 | A1 | 10/2011 | Bonhoeffer et al. | |
| 2012/0022639 | A1 | 1/2012 | Hacohen et al. | |
| 2012/0083874 | A1* | 4/2012 | Dale | A61F 2/2427 623/2.11 |
| 2012/0323316 | A1 | 12/2012 | Chau et al. | |
| 2013/0035759 | A1 | 2/2013 | Gross et al. | |
| 2013/0204357 | A1 | 8/2013 | Thill et al. | |
| 2013/0304200 | A1 | 11/2013 | McLean et al. | |
| 2013/0317603 | A1 | 11/2013 | McLean et al. | |
| 2014/0144000 | A1* | 5/2014 | Creaven | A61F 2/9525 29/505 |
| 2014/0180401 | A1 | 6/2014 | Quill et al. | |
| 2014/0207231 | A1 | 7/2014 | Hacohen et al. | |
| 2014/0277409 | A1 | 9/2014 | Bortlein et al. | |
| 2014/0331475 | A1 | 11/2014 | Duffy et al. | |
| 2014/0358224 | A1 | 12/2014 | Tegels et al. | |
| 2015/0005863 | A1 | 1/2015 | Para | |
| 2015/0039081 | A1 | 2/2015 | Costello | |
| 2015/0081000 | A1 | 3/2015 | Hossainy et al. | |
| 2015/0216661 | A1 | 8/2015 | Hacohen et al. | |
| 2015/0351906 | A1 | 12/2015 | Hammer et al. | |
| 2016/0030169 | A1 | 2/2016 | Shahriari | |
| 2016/0038280 | A1 | 2/2016 | Morriss et al. | |
| 2016/0151153 | A1 | 6/2016 | Sandstrom et al. | |
| 2016/0270910 | A1 | 9/2016 | Birmingham et al. | |
| 2016/0331529 | A1 | 11/2016 | Marchand et al. | |
| 2017/0172738 | A1 | 6/2017 | Kassas | |
| 2017/0181852 | A1 | 6/2017 | Kassas | |
| 2017/0216027 | A1 | 8/2017 | Marchand et al. | |
| 2017/0231761 | A1 | 8/2017 | Cohen-Tzemach et al. | |
| 2018/0055629 | A1 | 3/2018 | Oba et al. | |
| 2018/0147053 | A1 | 5/2018 | Tuval et al. | |
| 2018/0185142 | A1 | 7/2018 | Quill et al. | |
| 2018/0338832 | A1 | 11/2018 | Ganesan et al. | |
| 2019/0167421 | A1 | 6/2019 | Chau et al. | |
| 2019/0262129 | A1 | 8/2019 | Cooper et al. | |
| 2019/0321171 | A1 | 10/2019 | Morriss et al. | |
| 2019/0365538 | A1 | 12/2019 | Chambers et al. | |
| 2020/0315794 | A1 | 10/2020 | Quill et al. | |
| 2021/0000593 | A1 | 1/2021 | Rahmig et al. | |
| 2021/0196459 | A1 | 7/2021 | Marchand et al. | |
| 2021/0315691 | A1 | 10/2021 | Rahmig et al. | |

FOREIGN PATENT DOCUMENTS

| | | | |
|---|---|---|---|
| WO | WO-2012/178115 | A2 | 12/2012 |
| WO | WO-2015/107226 | A1 | 7/2015 |
| WO | WO-2018144971 | A1 * | 8/2018 |
| WO | WO-2018/197041 | A1 | 11/2018 |
| WO | WO-2019/158628 | A1 | 8/2019 |

OTHER PUBLICATIONS

International Search Report and Written Opinion for International Application No. PCT/EP2015/051037, mailed May 6, 2015 (9 pages).

International Search Report and Written Opinion for International Application No. PCT/EP2019/073768, dated Dec. 13, 2019 (10 pages).

International Search Report and Written Opinion for International Application No. PCT/EP2019/075216, dated Feb. 7, 2020 (10 pages).

International Search Report and Written Opinion for International Application No. PCT/EP2020/051955, dated Mar. 26, 2020 (12 pages).

* cited by examiner

A

DETAIL B

C

A

B DETAIL C

A

DETAIL D

B

A

DETAIL E

B

A

B

A

B

A

B

A

B

A

B

A

B

A

B

LOADING TOOL AND METHOD FOR LOADING A PROSTHESIS

The present invention relates to a heart valve prosthesis loading device and a method for loading a heart valve prosthesis onto a delivery system.

BACKGROUND

In the last decades minimally invasive techniques have advanced and are now possible in many medical fields.

In recent years the treatment of heart valve diseases and defects has become more and more successful. Examples are transapical, transjugular and transfemoral procedures for heart valve replacement therapies, e.g. aortic and mitral heart valve treatments.

In many cases a stent-based prosthesis with a tissue based replacement valve, e.g. pericard, is used and implanted to replace the endogenous heart valve by way of a catheter or delivery system.

The prosthesis has to be crimped and loaded onto the delivery system and a number of systems have been described in the art.

Known crimping devices work e.g. as follows: the transcatheter heart valve prostheses are crimped using a radial crimper or a set of funnels, through which the prostheses are pushed. Radial crimpers are utilized for stainless steel stents as they maintain their crimped state once the force of the radial crimper is released. Self-expanding nitinol stents usually get pushed through one or several funnels, which reduces their diameter. However, these stents are commonly laser cut stents. The rigid structure of a laser cut stent can transfer force in a longitudinal direction, without compressing. This is prerequisite to allow for pushing a stent through a funnel.

Braided structures included in stents or prostheses imply challenges that cannot be overcome by current crimping tools. A heart valve prosthesis containing a braided Nitinol stent—due to its self-expansion property—cannot be crimped without disadvantages by way of a radial crimper because the stent would expand again as soon as the force of the radial crimper is released. The prosthesis would have to be maintained in a crimped state in order to be able to advance a delivery system shaft over it. When applying a longitudinal force to a braided stent, as would be the case when pushing it through a funnel, the stent would get compressed longitudinally, rather than advanced through the funnel. This could induce damage to the braided structure. Compressing the prosthesis within the funnel would also not allow for proper crimping.

One problem in current crimping and loading tools is that forces are applied to the stent in order to crimp and load it onto a delivery system. This in turn can lead to damaging the tissue of the replacement valve with detrimental consequences for the functioning of the prosthesis in situ after deployment. Another problem is to achieve a symmetrical crimping and loading of the prosthesis which is difficult in view of the forces applied during the crimping procedure. Yet another problem is to achieve a small diameter in the crimped state without damaging not only the tissue valve but neither damage the stent component by way of non-symmetrical crimping or by way of non-symmetrical forces applied onto the stent component. Yet another problem arises if different stent materials or materials with different material characteristics due to different diameters or thickness dimensions or due to different structures or different foreshortening are used.

One example of a stent-based prosthesis is disclosed in WO2015/107226A1 including a Nitinol inner stent cut of a Nitinol tube and an outer stent of a braided Nitinol material wherein the pericard replacement valve is attached to the inner stent. Such a stent-based prosthesis is difficult to crimp and load onto a catheter due to its different material structures and characteristics.

Another example of a stent-based prosthesis is disclosed in WO2019/158628A1 which describes inter alia a laser cut in laser cut two part stent which may also be difficult to be crimped due to its flexible parts of inter alia the outer stent part.

Accordingly, it is one object to provide a crimping and loading device or assembly of parts reducing the disadvantages of the prior art or essentially avoiding these disadvantages.

It is another object to provide a crimping and loading device or assembly of parts useful for crimping and/or loading on a catheter a stent-based prosthesis which comprises at least two different stent material characteristics or/and two different stent materials, and which reduces the disadvantages of the prior art or essentially avoids these disadvantages.

It is another object to provide a method for crimping and/or loading a stent-based prosthesis which comprises at least two different stent material characteristics and/or two different stent materials, and which reduces the disadvantages of the prior art or essentially avoids these disadvantages.

It is another object to provide a method for crimping and/or loading a stent-based prosthesis which comprises a braided stent component, and which reduces the disadvantages of the prior art or essentially avoids these disadvantages.

BRIEF SUMMARY OF THE DISCLOSURE

In one aspect the disclosure relates to a loading device or an assembly of parts for crimping a stent or stent-based prosthesis from an expanded diameter to a compressed diameter comprising as components a funnel (102), a tubular structure (103) within a base part (106), a pulling means (104), and at least one pulling suture guidance hole (108) useful for passing through a pulling suture (105).

In one aspect the disclosure relates to an assembly of parts, a crimping device or/and a loading device for crimping a stent or stent-based prosthesis or/and loading a stent or stent-based prosthesis onto a delivery device comprising or consisting of or characterized by a conical or tapered means (e.g. a funnel) (102), a pulling means (104), and at least one pulling suture (105) releasable attached or in a manner that it can be dis or deconnected, e.g. cut, to the stent or stent-based prosthesis, preferably further characterized by a crimping suture (109) releasable attached to a prosthesis or in a manner that it can be deconnected, e.g. cut.

In another aspect the disclosure relates to a method for crimping or/and loading a stent, a stent-based prosthesis, or/and heart valve prosthesis onto a catheter or delivery system.

In another aspect the disclosure relates to a method for crimping or/and loading a stent or stent-based prosthesis from an expanded diameter to a compressed diameter using a tapered means and a pulling means.

In another aspect the disclosure relates to a method for crimping or/and loading a stent or stent-based prosthesis from an expanded diameter to a compressed diameter using a tapered means, a tubular structure and a pulling means.

In another aspect the disclosure relates to a method for crimping or/and loading a stent or stent-based prosthesis from an expanded diameter to a compressed diameter comprising the following steps: a. Connecting the stent or stent-based prosthesis to a pulling means by way of at least one pulling suture; b. Pulling the stent or stent-based prosthesis into a funnel; c. Pulling the stent or stent-based prosthesis through the funnel into a tubular structure whereby the diameter of the stent or stent-based prosthesis is compressed to a target diameter; d. advancing the outer catheter shaft over the stent or stent-based prosthesis.

In another aspect the disclosure describes a peel-off tube for use in loading specific structures which imply difficulty in correctly loading or are prone to damage by the loading device or a common loading procedure.

In another aspect the disclosure relates to a system comprising a loading device, a prosthesis and a catheter.

DETAILED DESCRIPTION

Figure 1:
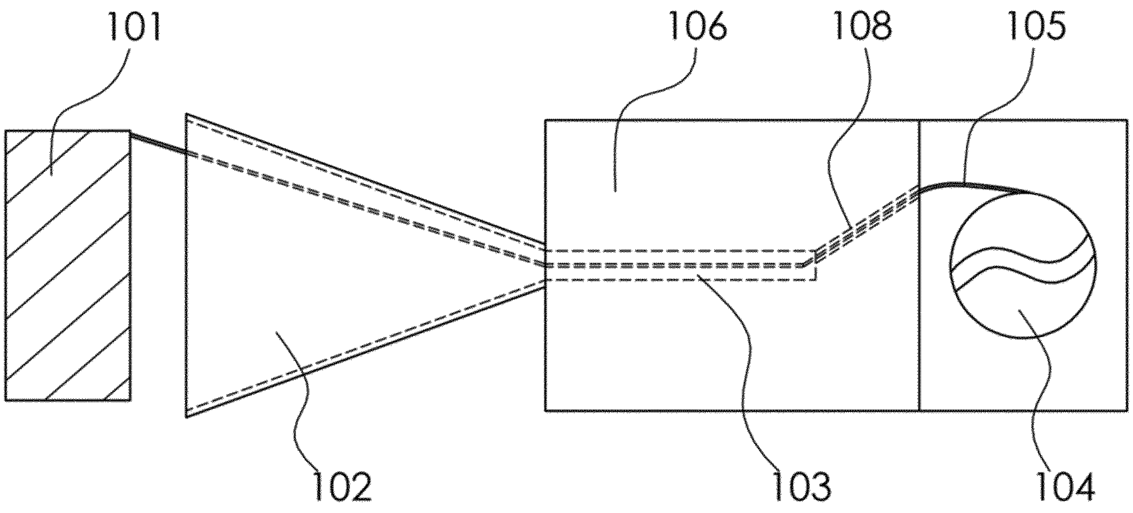
FIGS. 1-3 illustrate a loading sequence of a stent-based prosthesis.

In the following certain terms of the disclosure will be defined. Otherwise technical terms in the context of the disclosure shall be understood as by the applicable skilled person.

The term "prosthesis" in the sense of the disclosure is to be understood as a stent or stent-based prosthesis used interchangeably herein. The advantages of the assembly of parts and method of the disclosure are most evident with a prosthesis comprising a braided stent part and a valve made of biological tissue because the disclosure provides for an advantageous method producing very little to no negative impact when crimping or loading such a prosthesis. One example is a heart valve replacement prosthesis as described in WO2015/107226A1 or as described in WO2019/158628A1.

The term "assembly of parts", "crimping device" or "loading device" in the sense of the disclosure is to be understood as the parts used to compose the disclosed device and which parts are useful for either crimping the prosthesis or/and loading the prosthesis onto a catheter.

The term "catheter" or "delivery device" in the sense of the disclosure is to be understood as the device used to deploy a prosthesis in a patient at a determined site, e.g. to replace a heart valve like an aortic replacement heart valve, a mitral replacement heart valve or a tricuspid replacement heart valve, or a stent.

The term "funnel" in the sense of the disclosure is to be understood as any part useful to reduce the diameter of a stent or stent-based prosthesis and which has a conical or tapered area or is essentially a conical or tapered part. This part may have varying sizes and may be made out of different materials or comprise different materials as appropriate for its use. It may comprise low friction materials like polytetrafluorethylene (Teflon®).

The term "pulling means" in the sense of the disclosure is to be understood as any means or part useful to exhibit a pulling force to a suture, wire, stretch of material. It may be designed as a wheel or/and comprise means to reduce the forces needed to pull. It may also be combined with a motor to pull automatically and predetermined the total length or by stepwise fashion the e.g. suture to a predetermined point in the assembly of parts.

The term "releasable" in the sense of the disclosure is to be understood as the connection of two parts, e.g. base parts or sutures or sutures and stent or a prosthesis or areas of a prosthesis, which connection may be de-connected at a pre-determined point in time or during the method described herein. The connection may be designed in a way that it is accessible with an appropriate tool or is designed in a manner so that the connection may be opened to de-connect the two respective parts.

The term "crimping" in the sense of the disclosure is to be understood as reducing the diameter of the prosthesis from an expanded larger diameter to a compressed smaller diameter.

The term "loading" in the sense of the disclosure is to be understood as positioning a prosthesis onto a catheter in a manner so that the catheter is ready to initiate a delivery and deployment procedure to a patient.

The term "suture" in the sense of the disclosure is to be understood as a monofilament or braided structure, made out of a degradable (e.g. PGA, PLA, PGLA etc.) or non-degradable material (e.g. PE, PP etc.). A "pulling suture" can be made of any useful material, preferably wherein the pulling suture is made partially or essentially entirely of a tissue, a wire, a thread or filament, a metal, a metal wire or filament or thread.

The term "locking mechanism" in the sense of the disclosure is to be understood as any means which may connect and keep at least two parts together and allow for release and de-connecting said parts.

The term "mating cavity" in the sense of the disclosure is to be understood as an area which is designed to receive another part, e.g. the tip of a catheter, during the method disclosed herein.

The term "useful material" in the sense of the disclosure is to be understood as any materials that are compatible with each other and possibly can be sterilized and/or are low friction materials.

The term "un-covered" in the sense of the disclosure is to be understood as relating to the fact that a part introduced into the assembly of parts or connected therewith is not 100% covered by another part, e.g. by 1 to 30 mm or 2 to 20 mm or 5 to 10 mm, or which is not covered by about 1 to 35% or 2 to 20% or 5 to 15%.

The term "target diameter" in the sense of the disclosure is to be understood as a diameter which allows loading the prosthesis into the tubular structure or/and a diameter which allows the prosthesis to be loaded onto the catheter.

A "non-smooth surface" in the sense of the disclosure can be an additional diameter and can represent a step or tapered area which represents an additional diameter in the stent or prosthesis; a single piece can have non-smooth features or several pieces can be assembled so that they form a non-smooth surface and/or create one or more steps.

A "peel-off tube" in the sense of the disclosure can be an additional means to secure additional means of the prosthesis and make sure outwardly protruding means can be safely loaded. The peel-off tube can be easily taken of by way of a predetermined structuring of the device which allows for a directed peeling off in a predetermined direction, e.g. longitudinally. The peel-off means has an outer diameter which is smaller than the inner diameter of the outer shaft of the catheter system.

In one aspect the problem underlying the application is solved by an assembly of parts, a crimping device or/and a loading device comprising or consisting of or characterized by a funnel (102), a pulling means (104), possibly a tubular structure (103) and at least one pulling suture (105) releasably attached or deconnectably attached to a crimping suture (109) releasably attached to a prosthesis, or which can be cut for release (deconnection). Preferably wherein the crimping suture can be cut with suitable means.

In one aspect the problem underlying the application is solved by an assembly of parts, a crimping device or/and a loading device for crimping a stent or stent-based prosthesis or/and loading a stent or stent-based prosthesis onto a delivery device comprising or consisting of or characterized by a conical or tapered means, e.g. a funnel (102), a pulling means, e.g. a wheel (104), and at least one pulling suture (105) attached to the stent or stent-based prosthesis, preferably further characterized by a crimping suture (109) attached to a prosthesis and/or a tubular structure (103). Preferably wherein the crimping suture can be cut with suitable means.

In one aspect the problem underlying the application is solved by an assembly of parts for crimping a stent or stent-based prosthesis from an expanded diameter to a compressed diameter comprising as components a funnel (102), a tubular structure (103) within a base part (106), a pulling means, preferably a rotatable wheel (104), and at least one pulling suture guidance hole (108) useful for passing through a pulling suture (105).

The currently available crimping techniques and tools using radial compression and longitudinal push force are inappropriate for a braided stent structure and imply a number of disadvantages. The inventors now provide an advantageous solution by way of the current disclosure of a assembly of parts and/or a crimper and/or a loading tool or device which overcome the disadvantages or reduce at least the disadvantages of the known devices and methods by applying a novel and inventive crimping technique, which applies a longitudinal pull force.

The assembly of parts and/or a crimper and/or a loading tool according to the disclosure in one aspect contains a tubular element into which the prosthesis will be pulled during the loading procedure. Pulling the prosthesis into this tubular structure (103) will be facilitated by a pulling suture (105), which is connected to a rotatable wheel (104) on the assembly of parts. The prosthesis also has a suture around its circumference (109), which is connected to the before mentioned pulling suture (105) of the assembly of parts. Actuating a pulling means, e.g. a rotatable wheel, winds up the sutures and thus pulls the prosthesis (101) through a funnel (102) into the tubular structure. Once the prosthesis is within that tubular structure the delivery system shaft will be advanced over the prosthesis to maintain the crimped state. The suture will then be cut within the assembly of parts and removed from the prosthesis completely.

The assembly of parts (crimping/loading tool) thus overcomes the disadvantages of the state of the art at least partially or essentially completely. The braided stent component is kept symmetrical and it is now possible that it will be loaded symmetrically to the catheter; accordingly also damages to the tissue of the valve will essentially be avoided.

One advantage in particular, is that the suture which is used for pulling the prosthesis into the assembly of parts (crimping/loading tool) causes the braided stent to adopt a tapered/funnel-like shape. Consequently, the suture is the main trigger to crimp the prosthesis. The funnel only supports guiding the prosthesis into the tubular structure.

This is one difference in comparison to established crimping or loading systems, wherein often the funnel is the main trigger to force the prosthesis to its crimp diameter.

In a further aspect the assembly as described above further comprises at least one pulling suture (105), preferably two pulling sutures (105), connected to the pulling means (104), preferably wherein the pulling suture (105) is further releasably or non-releasably connected to a stent or stent-based prosthesis (101), preferably wherein the pulling suture(s) exhibit loops, more preferably a slideable knot, preferably wherein the pulling suture (105) is connected with a crimping suture (109).

In a further aspect the assembly as described above is characterized by a funnel (102) which is composed of at least two parts, preferably which parts are connected by a disengageable locking mechanism. E.g. the part can be longitudinally cut and can be assembled or it can be made of one part or can be composed of several parts.

In a further aspect the assembly as described above is characterized by further comprising a catheter releasably connected to the stent or stent-based prosthesis.

The assembly as described above can furthermore comprise at least 2 pulling sutures (105) and 2 pulling suture guidance holes (108 and 108'). It could also be 3, 4, 5, 6, 7, 8, 9, 10, 11, or 12 pulling sutures (105) and more than 2 pulling suture guidance holes.

In another aspect the assembly as described above can further comprise at least one pulling suture access hole, preferably two pulling suture access holes, which facilitate access to the sutures and through which they can be cut after the stent is pulled into the tubular structure and the catheter shaft is advanced. This allows for removal of the sutures from the stent after crimping.

Moreover, the assembly as described above can further comprise a catheter tip mating cavity. The tip mating cavity will be adapted in its design and dimensions depending on the catheter used together with the particular stent or stent-based prosthesis.

In another aspect the assembly as described above can further comprise a flared telescoping tube (113). This aspect may advantageously contribute to facilitate the crimping and/or loading procedure. It may also be advantageous to facilitate loading the proximal part (atrium directed) of the prosthesis, especially if the catheter has a stent holder.

The base part will be designed to fit the remaining parts of the assembly and depending on the particular features and characteristics. In one aspect the base part (106) is composed of at least two parts which are releasably connected.

The funnel (102) will also be adapted to the other parts and features and to the dimensions of the stent or stent-based prosthesis. Also the tapering may vary. The diameter is advantageously larger than the prosthesis outer diameter. The angle of the funnel can be 20 to 30°. In one aspect the funnel and the base part are releasably connectable. Also the funnel can be composed of one or more, e.g. two or three parts which may be connected and de-connected.

The assembly according to the disclosure herein will not only serve to crimp the stent or stent-based prosthesis but it will be designed in a manner to easily release the catheter with the loaded prosthesis. Accordingly, and where necessary the parts of the assembly will be connectable and detachable in order to facilitate the release procedure of the catheter. Accordingly, the assembly as described above is releasably connected with a catheter.

The stent or prosthesis can further comprise a non-smooth surface, e.g. one or more steps (115).

The assembly of parts can be made of any useful material known by the skilled person in this field, e.g. polytetrafluorethylene (PTFE). Preferably certain parts exposed to friction use a low friction material or are coated with such a material, e.g. PTFE/Teflon®. In particular the flared telescoping tube (113) can be made out of PTFE.

In one aspect the problem underlying the application is further solved by a method for crimping a prosthesis using a funnel (102), a pulling means and at least one pulling suture (105) releasably attached to a crimping suture (109) which is attached to a prosthesis and which sutures (105, 109) are detached from the prosthesis after crimping.

In one aspect the problem underlying the application is further solved by a method using an assembly of parts, a crimping device or/and a loading device for crimping a stent or stent-based prosthesis or/and loading a stent or stent-based prosthesis onto a delivery device comprising or consisting of or characterized by a conical means, e.g. a funnel (102), a pulling means, e.g. a wheel, and at least one pulling suture (105) releasably attached to the stent or stent-based prosthesis, preferably further a crimping suture (109) releasably attached to a prosthesis In one aspect the problem underlying the application is further solved by a method for crimping a stent or stent-based prosthesis from an expanded diameter to a compressed diameter comprising the following steps:

a. Connecting the stent or stent-based prosthesis (101) to a pulling means (104) by way of at least one pulling suture (105);
b. Pulling the stent or stent-based prosthesis into a funnel (102);
c. Pulling the stent or stent-based prosthesis through the funnel (102) into a tubular structure (103) whereby the diameter of the stent or stent-based prosthesis is compressed to essentially a target diameter;
d. preferably advancing the outer catheter shaft over the stent or stent-based prosthesis;
e. preferably cutting and removing all sutures in contact with the prosthesis;
f. preferably de-connecting the catheter carrying the prosthesis from the loading tool.

In an alternative embodiment a crimping suture for an additional/non-smooth stent feature (116) wraps directly around the crimped prosthesis/implant (101), particularly around an additional non-smooth stent feature (115).

In an alternative embodiment the crimping suture for an additional/non-smooth stent feature (116) wraps around a flared telescoping tube (113). By pulling the flared telescoping tube (113) out of the tubular structure (103) the crimping suture for an additional/non-smooth stent feature (116) is wrapped directly around the crimped prosthesis/implant (101); preferably crimping the additional/non-smooth stent feature below the inner diameter of the outer catheter shaft (107); and preferably advancing the outer catheter shaft partially or fully over the stent or stent-based prosthesis.

The same advantages as pointed out above for the assembly of parts will apply to the method and achieved by same mutatis mutandis.

In the method as described above the sutures may be connected to the stent or stent-based prosthesis by any useful means or manner. The pulling suture or crimping suture can e.g. split in several sutures, like two, three, four, five, six etc., which are releasable connected with the stent or stent-based prosthesis. The suture can also exhibit a special one or several means for connection to the stent or stent-based prosthesis. In one aspect the method as described above is characterized in that the at least one pulling suture (105) is connected to the stent or stent-based prosthesis by way of a crimping suture (109). The crimping suture may be attached or moved through the braid or any part of the stent. It may also represent a closed circle or two half circles releasable connected with the pulling suture. The sutures can be connected with means or knots known to the person skilled in the art, e.g. by a ball or a knot and a slideable knot (forming a loop).

In the method as described above the stent or stent-based prosthesis can be connected to the pulling means by way of at least one pulling suture, or e.g. two, three, four, five or six pulling sutures.

In another aspect of the method as described above the stent or stent-based prosthesis may be not completely covered by the tubular structure (103). In one aspect the stent or stent-based prosthesis remains un-covered over an axial area of 2 to 20 mm, or of 5 to 10 mm, or 1 to 35% or 5 to 15%.

After crimping and/or the loading is performed or as appropriate in the sequence of method steps the suture, e.g. the pulling suture and/or the crimping suture is cut or/and the suture(s) is (are) de-connected or removed from the stent or stent-based prosthesis.

The method as described above is further characterized in that the stent or stent-based prosthesis is further releasably connected with a catheter, preferably with a catheter tip, preferably wherein the guide wire shaft comprises a stent holder (114). It can be facilitated by a telescoping mechanism.

The catheter used to load the stent or stent-based prosthesis may be any catheter design useful for a particular stent or stent-based prosthesis. Accordingly, the method and parts as described above will be tailored to said catheter which is appreciated by the skilled person who knows how to adapt the current parts and method thereto. In one aspect in the method as described herein the outer catheter shaft is advanced over the stent or stent-based prosthesis.

The connections of the stent or stent-based prosthesis with the sutures can be de-connected by any useful means known in the art, e.g. by way of specific locking and un-locking members or the like. In one aspect of the method the sutures are cut and pulled out of the stent or stent-based prosthesis.

The method as described above can further comprise the steps of crimping the prosthesis partially into the tubular structure and onto the catheter. The section of the guidewire shaft with the stent holder remains outside of the tubular structure. The uncovered section of the prosthesis is crimped onto the stent holder of the catheter by pulling the flared telescopic tube (113) out of the base, before or after removing the funnel (102). The outer shaft is advanced over the stent or stent-based prosthesis and the remaining loading tool components are removed from the catheter.

In the method as described herein the assembled parts and the catheter may self-align or manually be positioned correctly in each step of the method as useful. In one aspect the method as described herein comprises the step wherein prior to the crimping of the stent or stent-based prosthesis the catheter shaft is placed essentially within the center of the stent or stent-based prosthesis.

The sequence of the method steps is aligned with the parts of the assembly and the logic of crimping and/or loading the stent or stent-based prosthesis onto the catheter. Accordingly the logic of the method and the method steps depends on the particular part design. In one aspect the method as described above is characterized in that prior to the crimping of the stent or stent-based prosthesis the catheter tip is placed within the base (106).

In alternative embodiments the disclosure relates to means for more smoothly loading a prosthesis onto a catheter. This may be necessary if non-smooth surfaces are comprised or/and steps (115) are present in the prosthesis. A means and process step is provided to achieve an easy and correct loading, e.g. a crimping suture for the additional/non-smooth stent feature (116) is wrapped around the flared telescoping tube (113) and both suture ends are tied to rotatable pins (117) on either side of the loading system. Rotation of one of the two pins (117) leads to winding up of the suture and thereby crimping the additional/non-smooth stent feature below the inner diameter of the outer catheter shaft (107). Once that is achieved, the outer catheter shaft (107) is advanced over the prosthesis/implant (101) up until the crimping suture of the additional/non-smooth stent feature. At this point about half of the additional/non-smooth stent feature is covered by the outer catheter shaft. The crimping suture for the additional/non-smooth stent feature (116) can be cut and removed from the prosthesis/implant (101). The outer catheter shaft (107) can then be fully advanced over the prosthesis/implant.

In an alternative embodiment of the disclosure another option is to have a smaller flared tube (118) within the base (106) of the loading system. This means that the inner diameter of the ‘smaller flared tube’ (118) is lower than the inner diameter of the outer catheter shaft (107). Hence the distal half of the additional/non-smooth stent feature (115) gets pulled into the smaller flared tube (118) and thereby crimped below the inner diameter of the outer catheter shaft (107). The outer catheter shaft is advanced over the proximal half of the additional/non-smooth stent feature. The smaller flared tube is a so-called peel-away tube. Step-wise the tube is peeled off while the outer catheter shaft is advanced over the prosthesis/implant (101).

In addition or as an alternative also a radial crimper (119) can be utilized to further radially reduce the diameter of the additional/non-smooth stent feature (115).

Thus it can be advantageously achieved to smoothly load a more complex prosthesis onto a catheter.

Another aspect of the disclosure is a peel-off means, e.g. a peel-off tube which will facilitate the loading of additional stent features like anchoring features by way of holding them during the loading procedure and which include a simple mechanism to take it off before finalization of the crimping procedure.

Such an additional means will also be advantageous in preventing or minimizing negative side effect from the loading procedure wherein materials of the catheter will be scraped off and lead to embolic incidents. Also stent features which imply parts protruding outwardly will thus be protected from damage during the loading procedure. Also it can be achieved now that all stent parts can easily be loaded completely into the catheter system.

In another aspect the disclosure relates to a system comprising an assembly as described above, a prosthesis and preferably a catheter.

The following examples will further illustrate the disclosure wherein the skilled person will understand that these examples are not meant to be restricting in any sense.

EXAMPLES

The following is a description of preferred aspects of the disclosure and it shall not be construed to be limiting in any aspect or manner. Moreover, the skilled person will appreciate that any aspect and feature of the disclosure herein above and below can be used and combined with any of the remaining features as disclosed herein. The disclosure shall be understood that any such feature can be combined with any other feature as disclosed herein without being in any sense bound or to be restricted in terms of combination of features.

The sequence of crimping the prosthesis and loading can be divided into three major steps: assembly of the assembly of parts and the prosthesis, the partially crimped state and the fully loaded state. It is possible to crimp and load a prosthesis as disclosed in WO2015/107226A1 and a prosthesis as described in WO2019/158628A1 which disclosure is entirely incorporated herein by reference. Hence, the loading of braided mesh stents of one or two parts and also of one or more parts laser cut stents can be facilitated by the device according to the disclosure.

In a first step (Loading System Setup) the parts and prosthesis are assembled for the method of crimping/loading:

The rotatable wheel is assembled to the base. The funnel is connected to the base as well, but can be removed at a later stage of the loading process. The pulling suture is connected to the rotatable wheel and guided through the tubular structure and the funnel to the prosthesis. There it is connected through the crimping suture (109) to the prosthesis (see FIG. 1).

Figure 2:
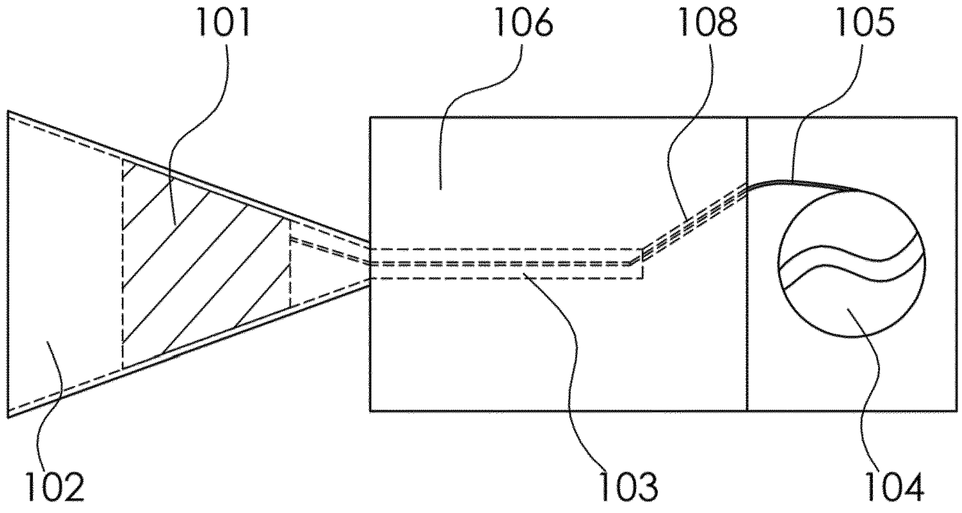

The Second Step is the Partially Crimped State:

When turning the rotatable wheel (104), the suture will be wound up around the wheel. The tension on the suture pulls the prosthesis (101) into the funnel (102). As mentioned before the suture already causes the prosthesis to take a funnel-like shape. The funnel is not required for that. The funnel just aids in guiding the prosthesis into the tubular structure (103) (see FIG. 2).

Figure 3:
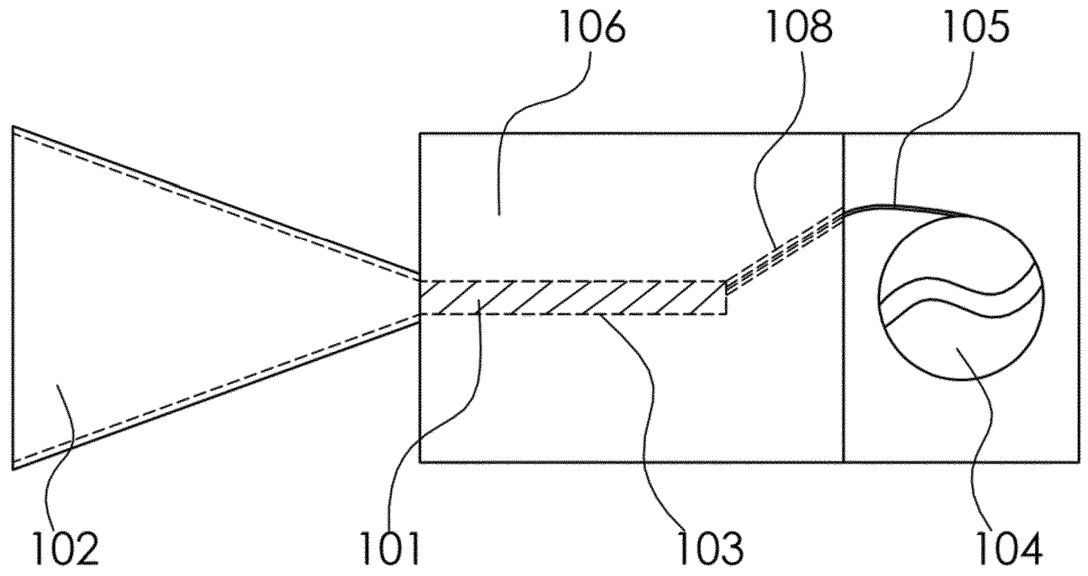

Finally the Prosthesis is in the Fully Loaded State:

The base and the tubular structure must be transparent to allow for visual guidance to see once the prosthesis hits the stop within the tubular structure. At that point no more rotation is required. The rotatable wheel and the base are connected through a special mechanism, which prevents unwinding of the wheel due to the tension on the suture. The tension on the suture is maintained due to that mechanism and the prosthesis will not slide/jump out of the tubular structure (see FIG. 3).

Figure 4:
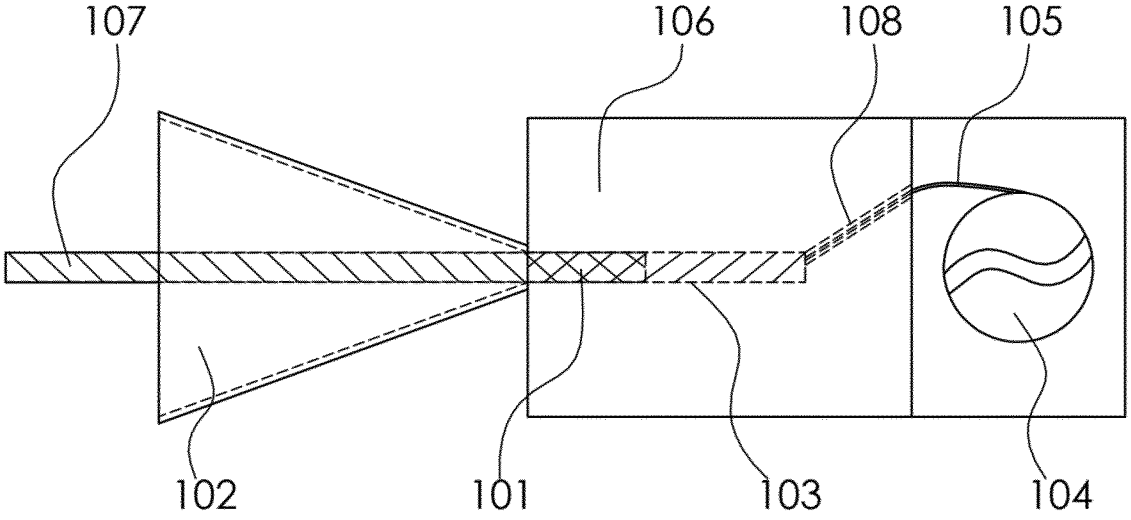
FIGS. 4-6 illustrate advancing of the catheter and alignment with the stent-based prosthesis, supported by adjustments to the tubular structure length.

After pulling the prosthesis completely into the tubular structure within the base, the outer catheter shaft is advanced and is aligned correctly with the prosthesis and loaded onto it. Outer catheter shaft (107) is advanced (see FIG. 4).

Figure 5:
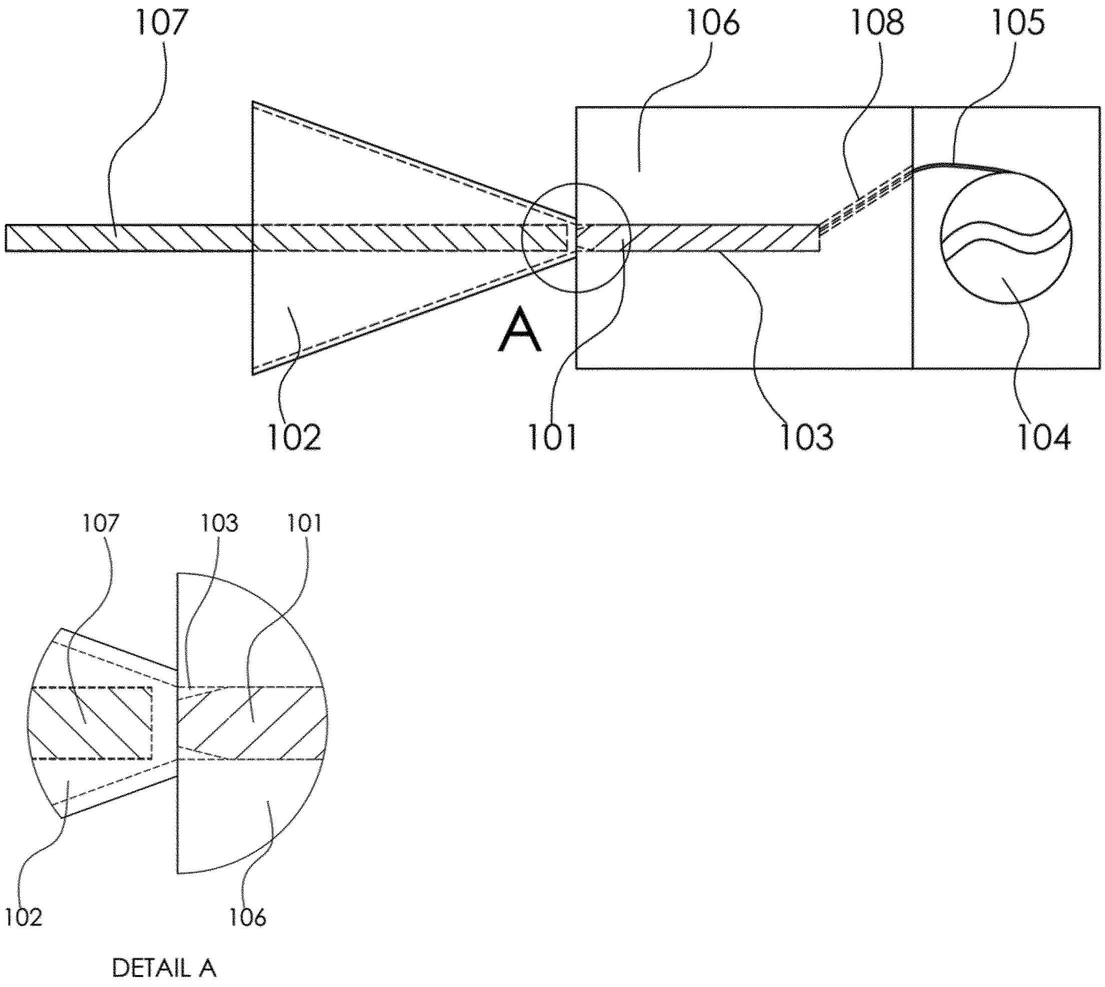

FIG. 5 and detail/close up A shows in detail the advancing of the outer catheter shaft and alignment with the crimped prosthesis. Specific to a prosthesis according to WO2015/107226A1 is that the atrial section of the stent tapers down when it is crimped. This aids in advancing the outer catheter shaft over the prosthesis. In an alternative embodiment the crimping can be performed without tapering down and the procedure is performed under careful visual control.

Figure 6:
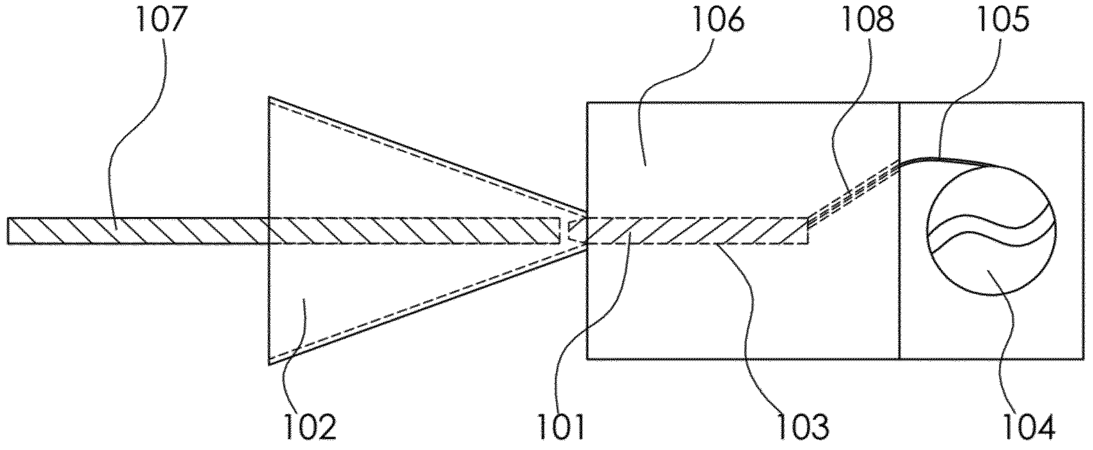
Figure 6:
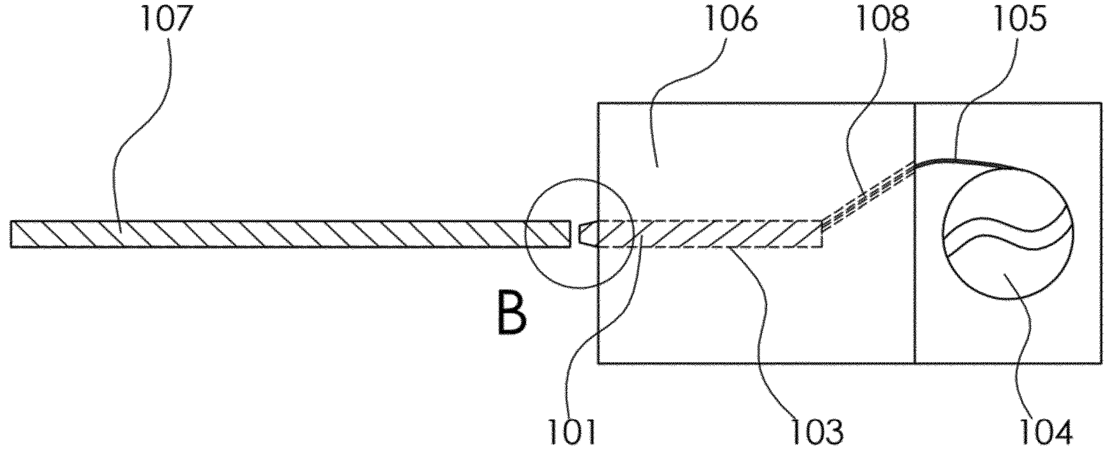
Figure 6:
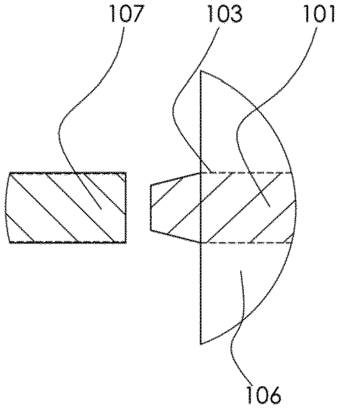

FIG. 6 shows a close up of advancing the outer catheter shaft of the prosthesis with a shortened base. If the crimped length of the prosthesis is e.g. 65 mm, the tubular structure is chosen to be 60 mm long. With 5 mm of the prosthesis exposed from the base and after removal of the funnel, visual control is ensured for a correct procedure and positioning. The outer catheter shaft can be carefully advanced over the prosthesis. This detail is also obvious from detail/close up B.

Figure 7:
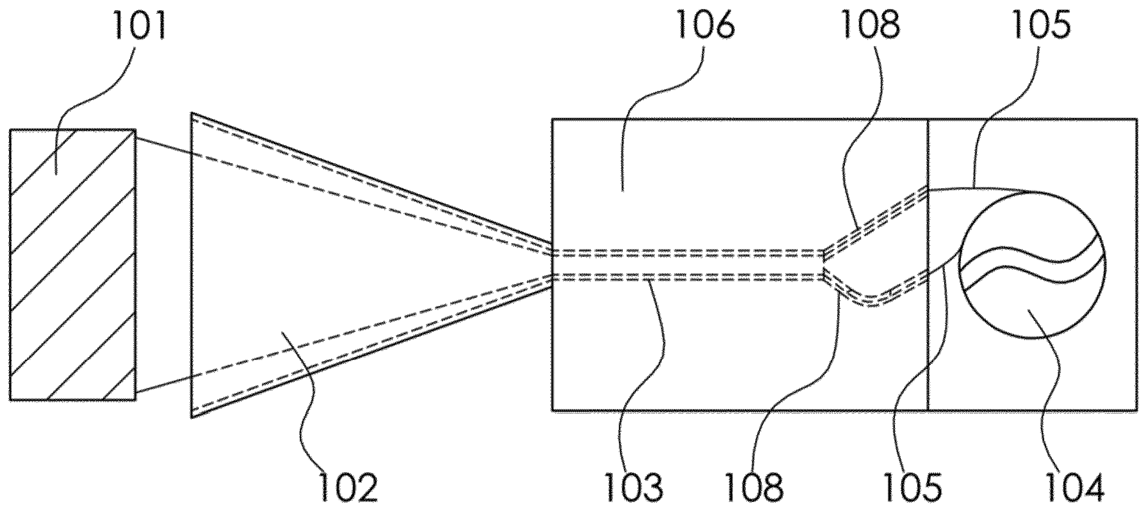
FIGS. 7-9 illustrate a two pulling suture device and connection of the pull suture with the crimping suture.

FIG. 7 depicts an alternative embodiment with two sutures for crimping and loading. The loading system is a configuration in which it has two suture guidance holes and two pulling sutures and suture ends, which are connected to the prosthesis. This ensures that the prosthesis is pulled even more evenly into the loading system. No manual adjustment to align the prosthesis properly is required.

Figure 8:
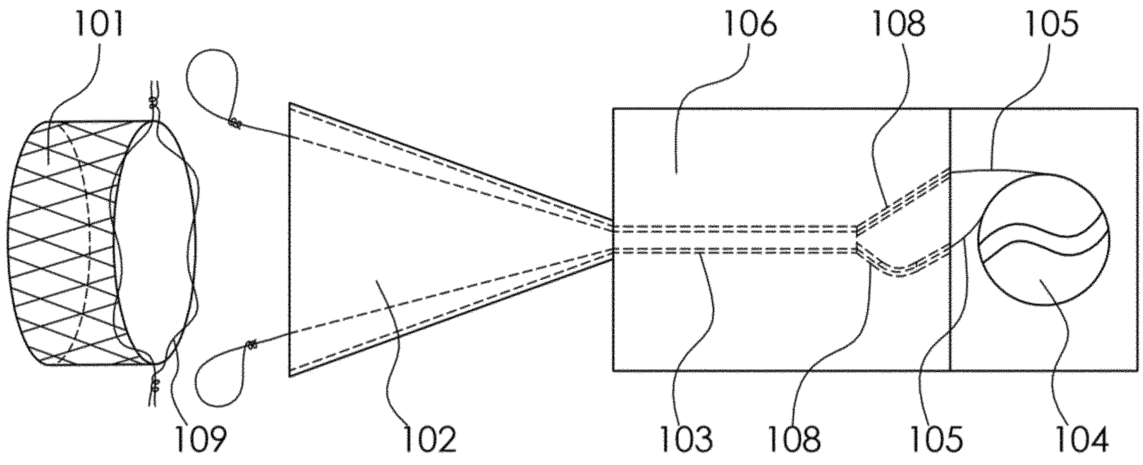

FIG. 8 shows the connection of the loading tool pulling sutures (105) and the crimping suture (109) of the prosthesis. The connection between the loading system and the prosthesis is effected by way of a combination of sutures (105, 109). Two sutures are threaded through the braided stent of the prosthesis. Each suture runs through half the circumference. The ends of both sutures are connected on both sides through knots. The loading system contains a suture, which on both ends has adjustable loops through slideable knots. These loops will be places around the knots of the prosthesis and the loops will be tightened. Once the loops are tightened, they cannot slip over the knots anymore.

Figure 9:
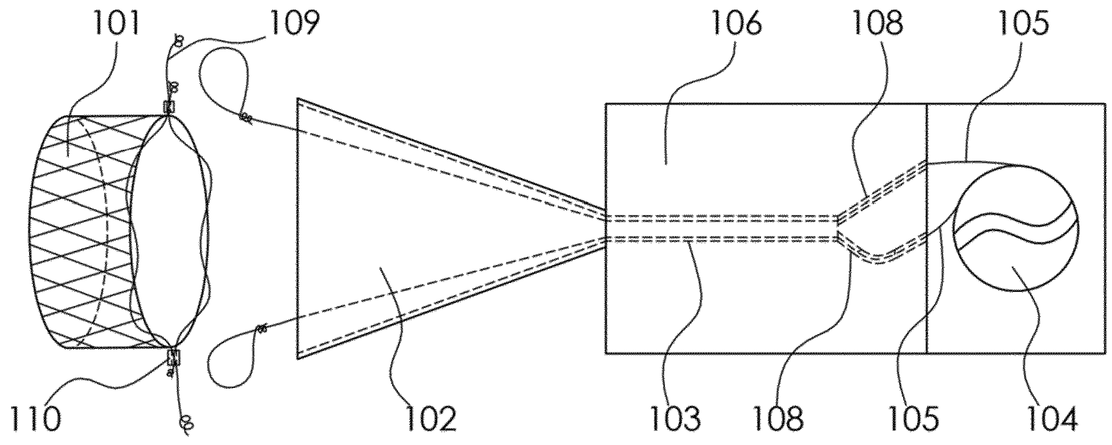

An alternative embodiment of the connection is depicted in FIG. 9. Again two sutures are threaded through the braided stent of the prosthesis—each running through half the circumference of the stent. The ends of the two sutures are then guided through a little tube/sphere etc. Each end of the two sutures will be tied in a knot, which is so big that it cannot slip through the hole of the tube. The two sutures are not connected to one another. The suture loops of the loading system are placed around one knot each. The loops should not pull on the same suture, but each on a different one. Once tension is applied to the sutures, through rotation of the wheel, the knots force the tubes against the prosthesis. Due to that the two sutures are being held closely together, which prevents separation of the braid wires of the stent. This is potentially even less harming to the stent. On a practical level the different sutures can be color coded. A green and a white suture are guided through half the circumference each. When pulling on the white suture on side and the green suture on the other side, the knots of each suture on their opposite side, force the tube against the prosthesis. Since both suture run through the tube, they are being held together (based in tube inner diameter) and prevent separation of the braid wires.

Figure 10:
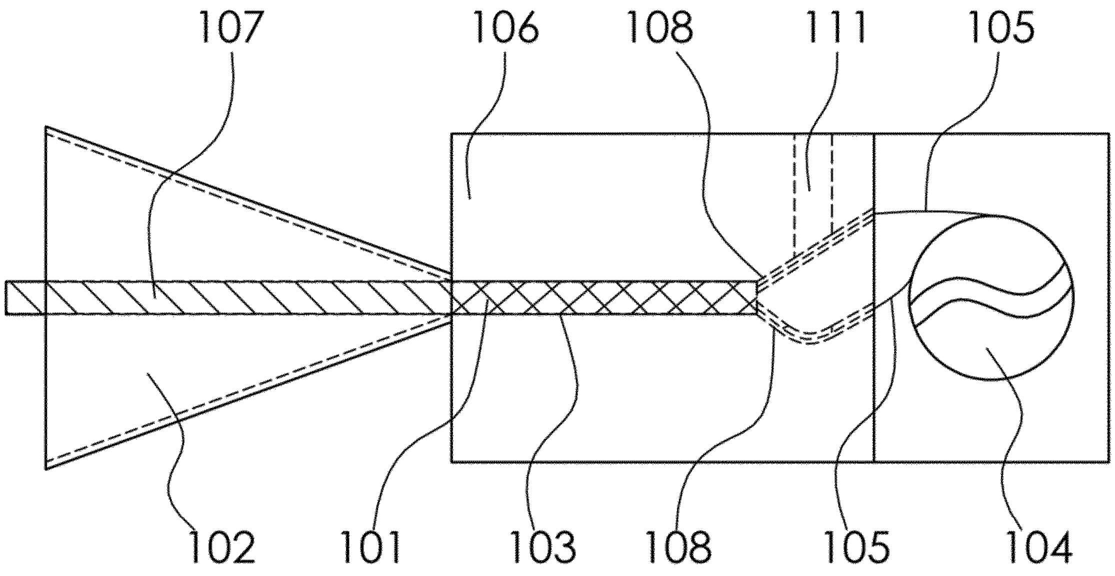
FIG. 10 illustrates the additional feature of a suture access hole.

FIG. 10 shows another detail useful for release and cutting of sutures when no longer necessary. One or more access holes (111) are provided in the device and used to cut sutures. Once the prosthesis is fully loaded and the outer catheter shaft is advanced over the prosthesis, the suture can be cut through the suture access hole. Further rotation of the wheel will pull the suture out of the prosthesis. This is procedure is true for the connection without the tubes. With the tubes, both suture guidance holes would need to be accessible through suture access holes. The sutures would need to be cut on both sides and the remaining sutures and tubes would need to be removed manually.

Figure 11:
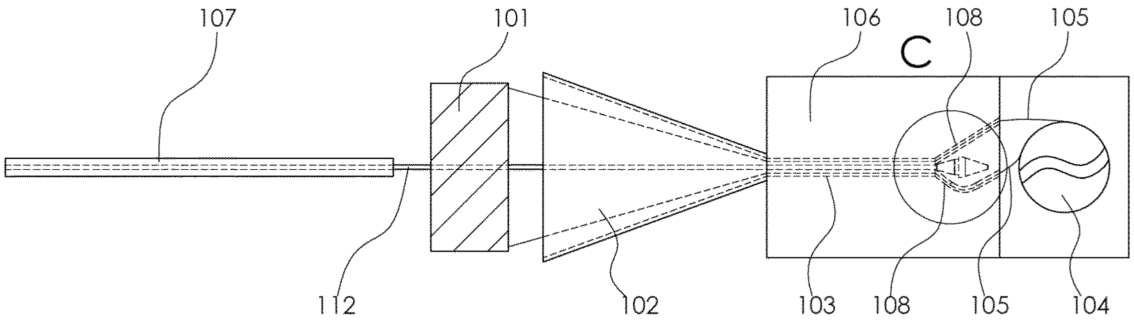
FIGS. 11-14 illustrate the loading sequence related to a catheter with a tip and/or stent holder.
Figure 11:
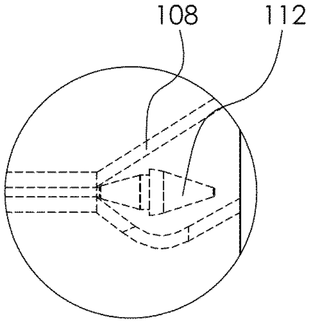

FIG. 11 depicts another detail: the loading system exhibits cavities for a guide wire shaft and tip of the catheter (112). A catheter usually consists of several concentric tubes. The outer shaft is the one, which maintains the crimped state of the prosthesis. Usually there is at least one more shaft, the smaller guidewire shaft. In the course of the procedure the guidewire shaft tracks the catheter over the guidewire. The tip of the catheter is bonded to the distal end of the guidewire shaft. To accommodate for such a catheter, the loading system would have mating cavities into which the tip fits. The base would have a bottom and a top piece, which are split in half so that the catheter with its tip can be placed inside. The loading system is mounted on/around the catheter. With that the prosthesis gets crimped directly onto the catheter.

Figure 12:
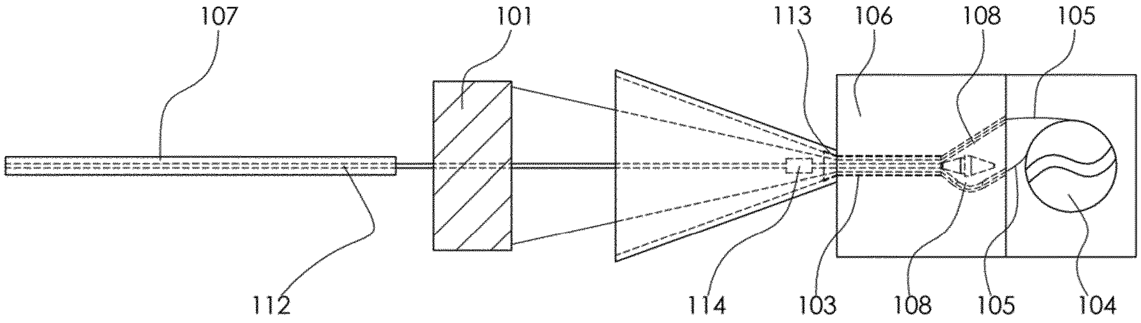

FIG. 12 depicts a loading system including a telescoping mechanism to accommodate for a stent holder. When using a two-step deployment mechanism the following feature is useful. Once the first deployment step is carried out, the design of the catheter has to ensure that premature deployment of the second part is prevented. For that purpose, there is a stent holder (114) on the catheter. The stent holder presses the atrial stent section against the outer catheter shaft and thus increases friction. The gap between the stent holder and the outer shaft is therefore very small. The prosthesis cannot be pulled into the loading system past the stent holder. The following version of the loading system, which contains a telescoping mechanism, accommodates for that. Assuming that the prosthesis is for instance 65 mm long in a crimped state, the tubular structure of the loading system (103) is only 40 mm long. In this case it also contains a flared tube (e.g. out of PTFE).

Figure 13:
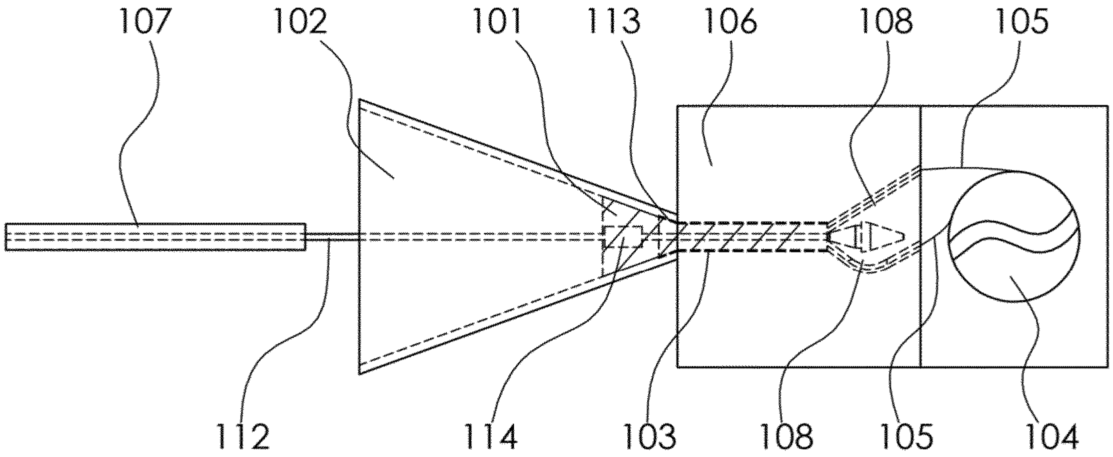

When the prosthesis is pulled into the loading system, only 40 mm are within the tubular structure. The rest is still within the flared section of the telescoping tube and the funnel (see FIG. 13).

Figure 14:
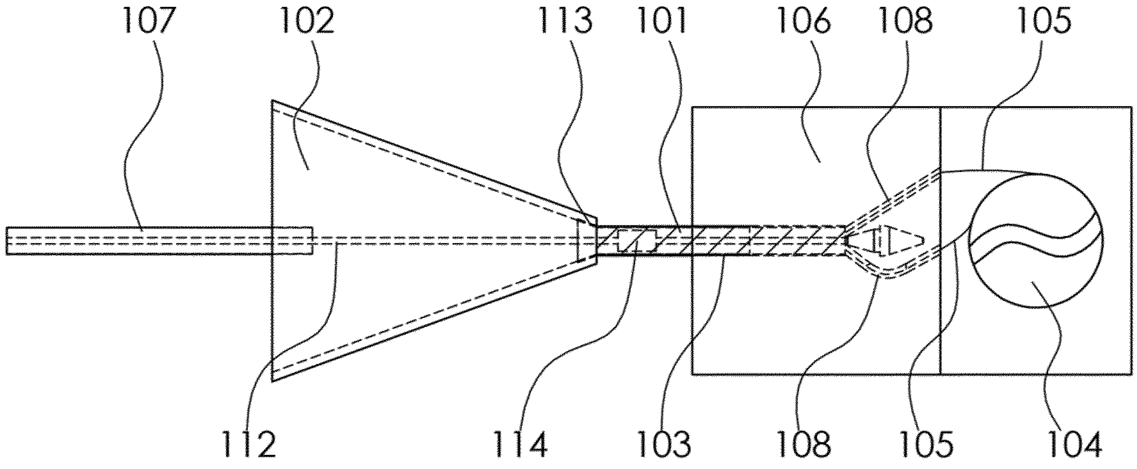
Figure 15:
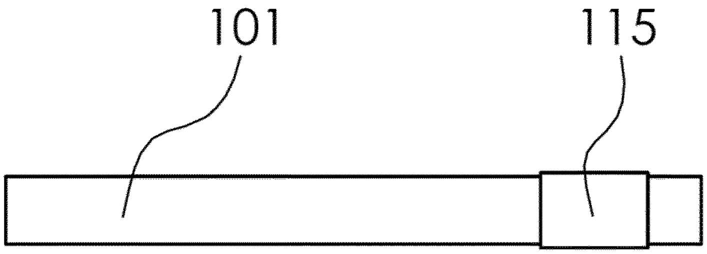
FIG. 15 describes a prosthesis/implant (101) which has a non-smooth surface. A single piece can have non-smooth features or several pieces can be assembled so that they form a non-smooth surface/create steps (115).
Figure 16:
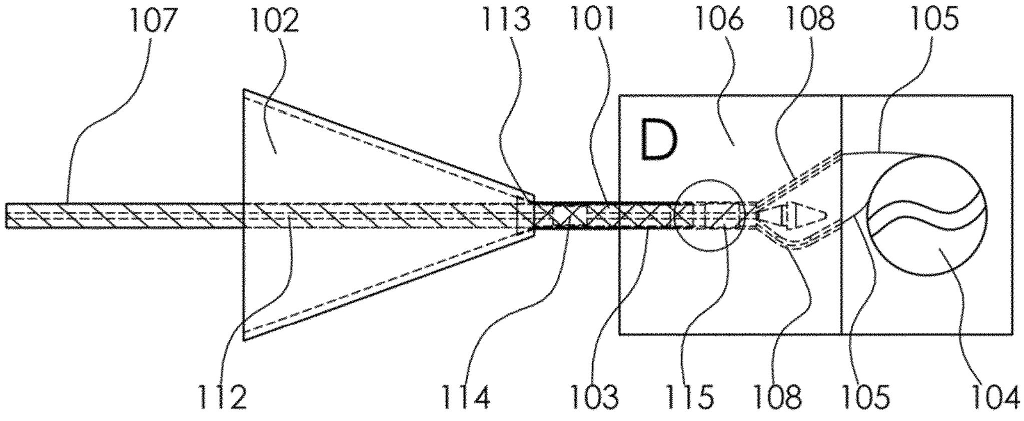
FIGS. 16 A and B (Detail D): the Figures illustrate that the loading procedure can be carried out as described above up until the point where the outer catheter shaft (107) is advanced over the prosthesis (101). At this point the outer catheter shaft (107) would get stuck at the step of the additional/non-smooth stent feature (115) as depicted.
Figure 16:
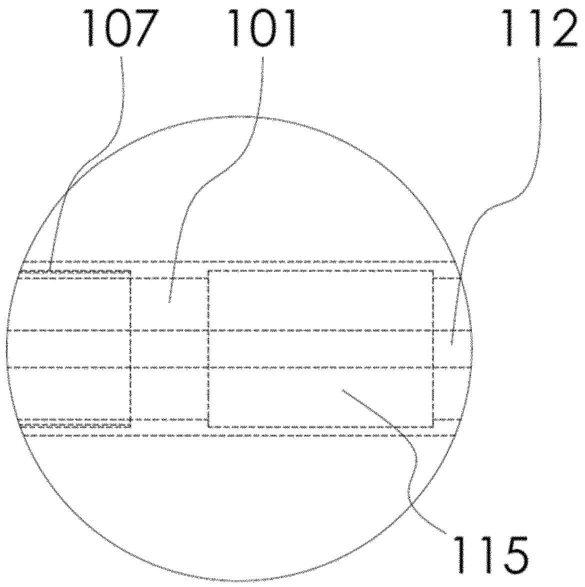
Figure 17:
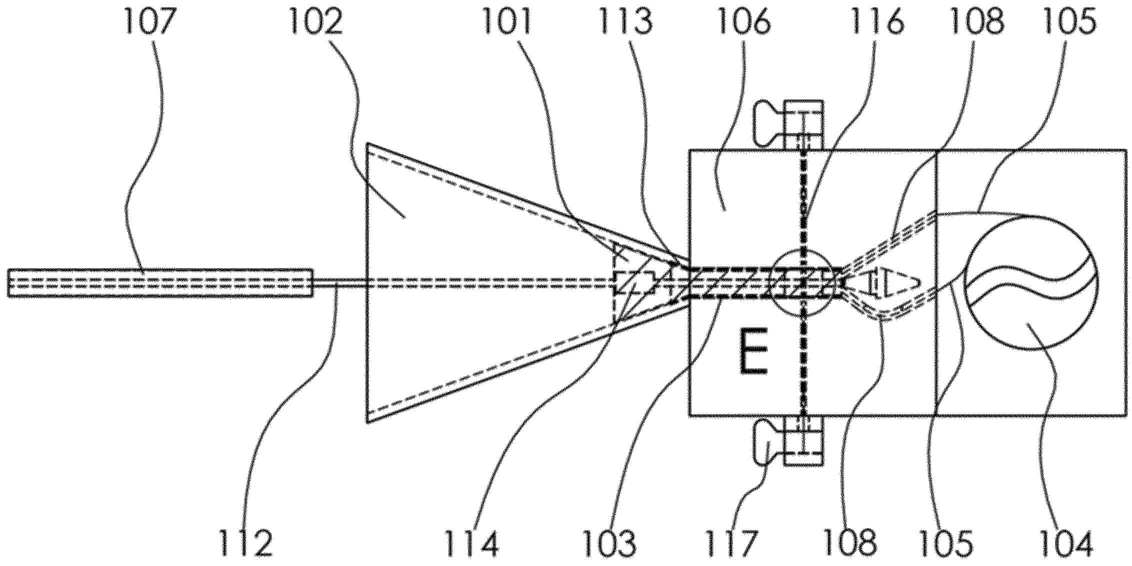
FIGS. 17 A and B (Detail E): the Figures illustrate that for the outer catheter shaft (107) to be able to get advanced over the prosthesis/implant (101), the additional/non-smooth stent feature, which has the greatest outer diameter (OD), needs to be crimped further to eliminate the step. For this purpose, a crimping suture for the additional/non-smooth stent feature (116) is wrapped around the flared telescoping tube (113) and both suture ends are tied to rotatable pins (117) on either side of the loading system.
Figure 17:
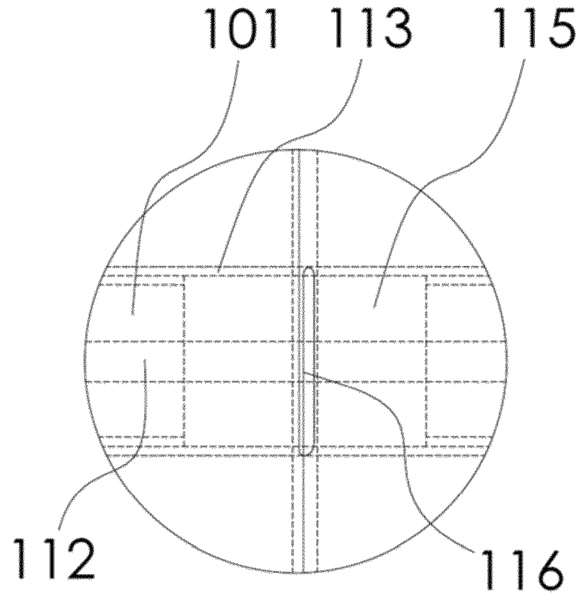
Figure 18:
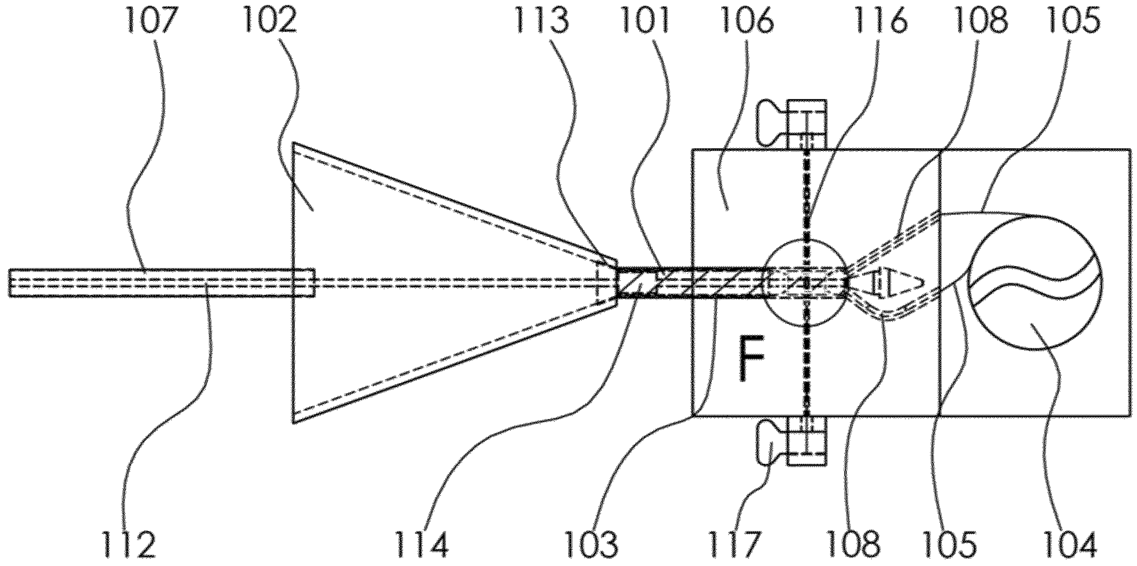
FIGS. 18 A and B (Detail F): the Figures illustrate that once the flared telescoping (113) tube is pulled out of the base (106) of the loading system, the crimping suture for the additional/non-smooth stent feature (116) wraps directly around the crimped prosthesis/implant (101), particularly around the additional non-smooth stent feature (115). Rotation of one of the two pins (117) leads to winding up of the suture and thereby crimping the additional/non-smooth stent feature below the inner diameter of the outer catheter shaft (107). Once that is achieved, the outer catheter shaft (107) is advanced over the prosthesis/implant (101) up until the crimping suture of the additional/non-smooth stent feature. At this point about half of the additional/non-smooth stent feature is covered by the outer catheter shaft.
Figure 18:
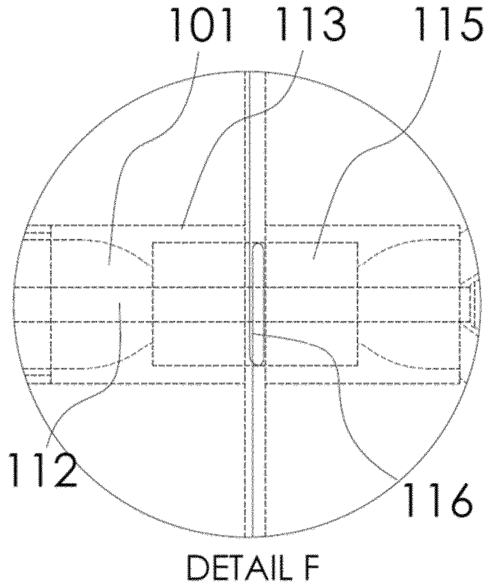
Figure 19:
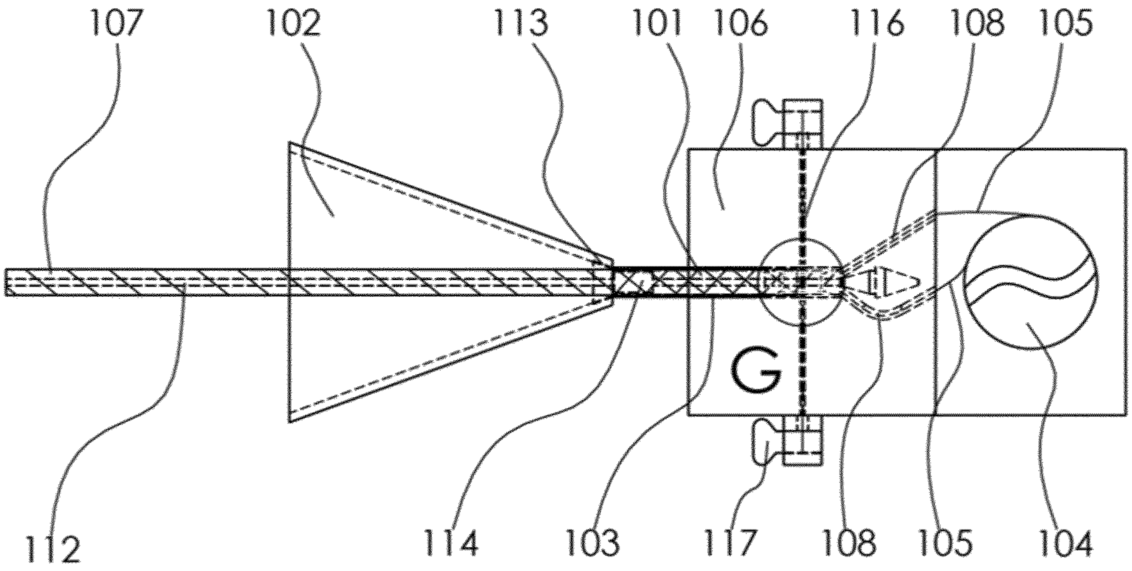
FIGS. 19 A and B (Detail G): the Figures illustrate in an alternative embodiment wherein the crimping suture for the additional/non-smooth stent feature (116) gets cut and removed from the prosthesis/implant (101). The outer catheter shaft (107) can then be fully advanced over the prosthesis/implant.
Figure 19:
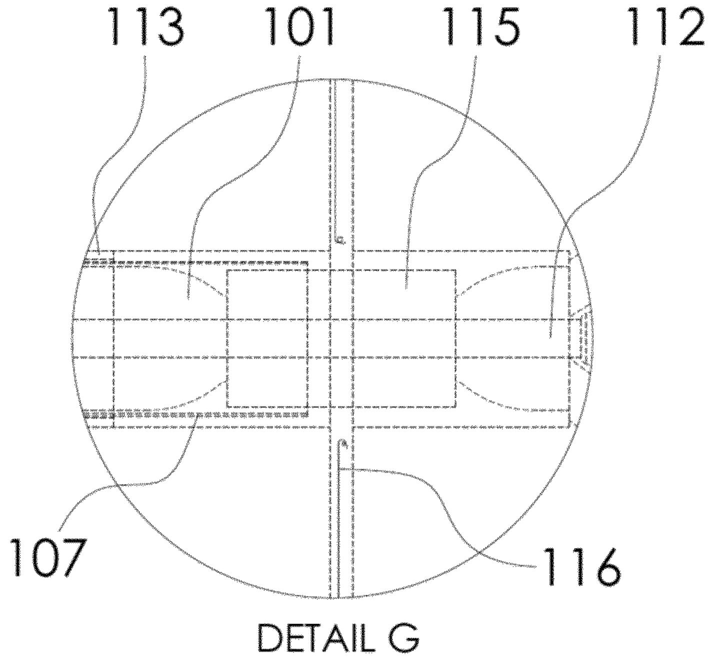
Figure 20:
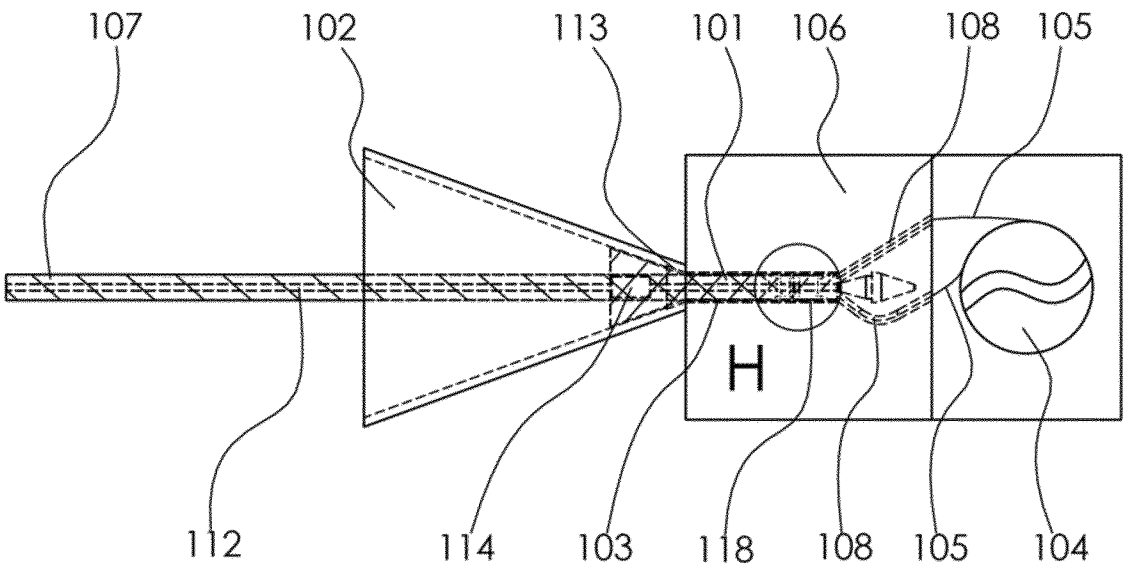
FIGS. 20 A and B (Detail H): the Figures illustrate in an alternative embodiment that another option is to have a smaller flared tube (118) within the base (106) of the loading system. This means that the inner diameter of the 'smaller flared tube' (118) is lower than the inner diameter of the outer catheter shaft (107). Hence the distal half of the additional/non-smooth stent feature (115) gets pulled into the smaller flared tube (118) and thereby crimped below the inner diameter of the outer catheter shaft (107). The outer catheter shaft is advanced over the proximal half of the additional/non-smooth stent feature. The smaller flared tube is a so-called peel-away tube. Step-wise the tube is peeled off while the outer catheter shaft is advanced over the prosthesis/implant (101).
Figure 20:
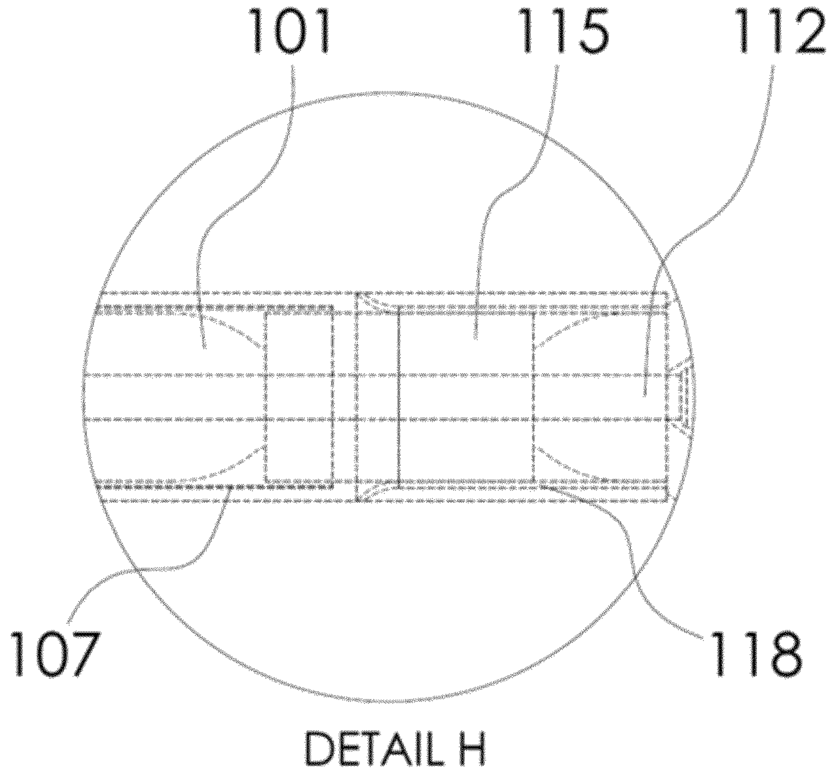
Figure 21:
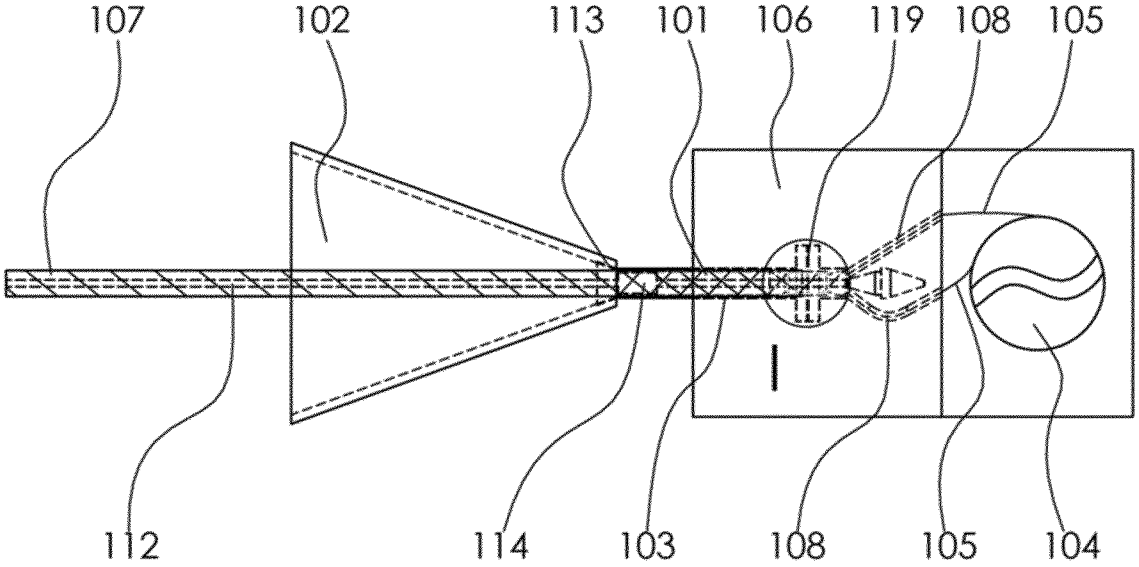
FIGS. 21 A and B (Detail I): the Figures illustrate that instead of the previously described suture, also a radial crimper (119) can be utilized to further radially reduce the diameter of the additional/non-smooth stent feature (115).
Figure 21:
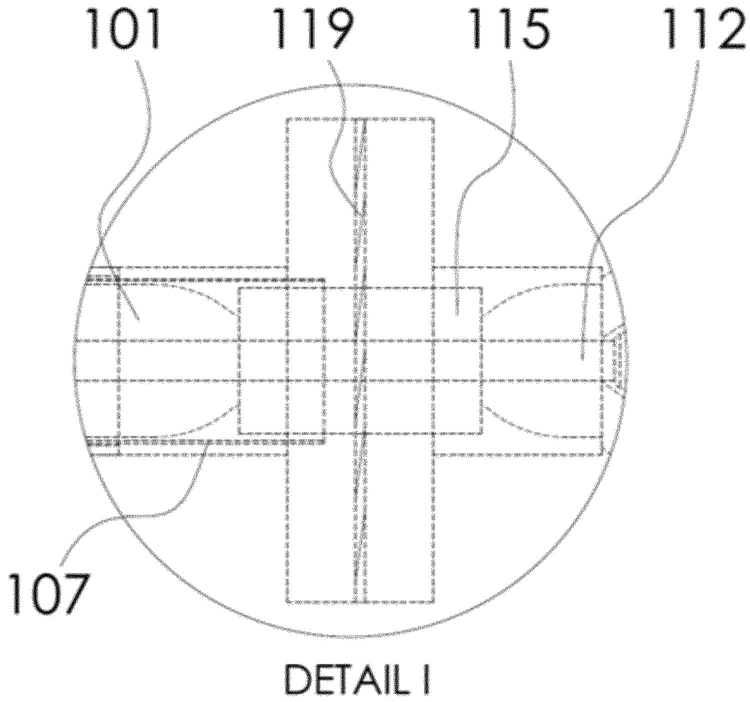

FIG. 14 depicts when the flared telescopic tube is pulled out of the base (with or without funnel). This crimps the remaining part of the prosthesis onto the stent holder. After that the outer shaft will be advanced over the prosthesis. The funnel can be removed for that step to allow for better visual control. Afterwards the suture will be cut and removed from the prosthesis. While keeping the tension on the sutures during the telescoping motion of the flared tube, it is ensured that the prosthesis will not be pulled out of the loading system.

FIGS. 15 to 21 describe a prosthesis/implant (101) which has a non-smooth surface. A single piece can have non-smooth features or several pieces can be assembled so that they form a non-smooth surface/create steps (115) and other advantageous features of a loading system and loading procedure according to the disclosure.

FIGS. 22 to 28 describe a prosthesis (101) according to the disclosure which can have one or more outwardly protruding features, e.g. anchoring features (115). These will still want to protrude outwardly even after crimping the stent and which may imply loading and releasing issues if not addressed properly with a particular means used to make sure that such features (115) do not interfere with the loading procedure. Here the use of a peel-off tube has been proven to be advantageous.

Figure 22:
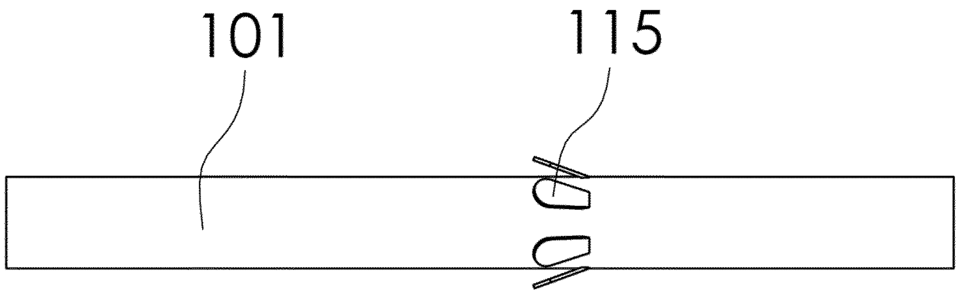
FIG. 22: the Figure describes a prosthesis (101) according to the disclosure which can have one or more outwardly protruding features, e.g. anchoring features (115). These will still want to protrude outwardly even after crimping the stent and which may imply loading and releasing issues if not addressed properly with a particular means used to make sure that such features (115) do not interfere with the loading procedure.

In particular in FIG. 22 the prosthesis (101) can have one or more outwardly protruding features, e.g. anchoring features (115). These will still want to protrude outwardly even after crimping the stent.

Figure 23:
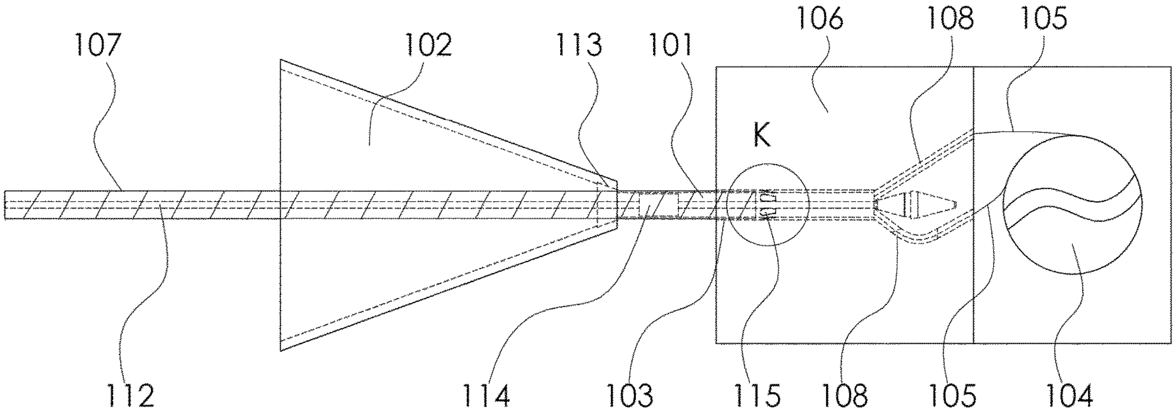
FIGS. 23 A and B: the Figures describe the issue when loading a prosthesis having particular protruding features like anchoring features (115). While the main section of the prosthesis/implant (101) is crimped inside the tubular structure, the anchoring features protrude outwards and would counteract the outer catheter shaft when trying to sheath the prosthesis/implant.
Figure 23:
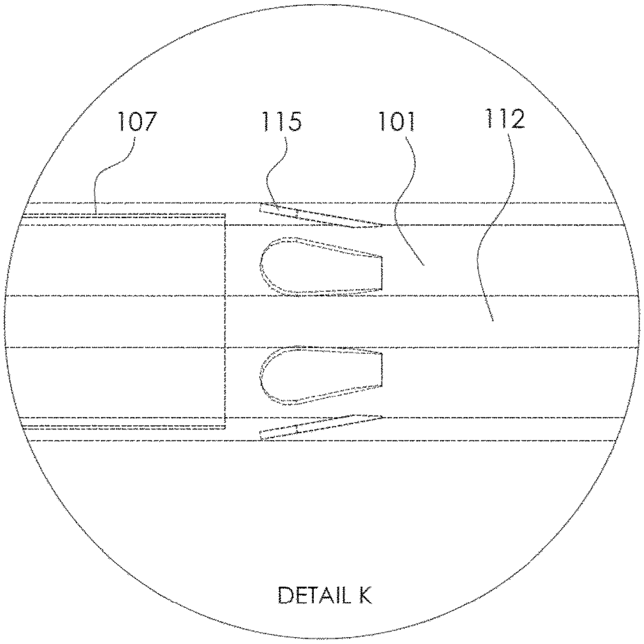

As is described in FIG. 23 the prosthesis is crimped into a tube or tubular structure (103), which has an inner diameter that is slightly larger than the outer diameter of the outer catheter shaft (107). After the prosthesis is crimped into the tubular structure the outer catheter shaft is advanced over the prosthesis. The outer catheter shaft thereby crimps the prosthesis down to its final crimp diameter, which is an additional two times the wall thickness of the outer catheter shaft. This can only be achieved if the prosthesis exhibits a smooth surface.

In case of outwardly protruding features/anchoring features (115) the outer catheter shaft would get stuck on these and cannot complete the crimping (see FIG. 23 and detail K). Forcing the outer catheter shaft over the anchoring feature can result in damage to the outer catheter shaft, such as delamination, braid wire exposure, split tip etc. On the other side it can also lead to permanent damage of the outwardly protruding feature or anchoring feature, which than negatively effects the durability of the device or does not allow it to perform its intended use/function.

Figure 24:
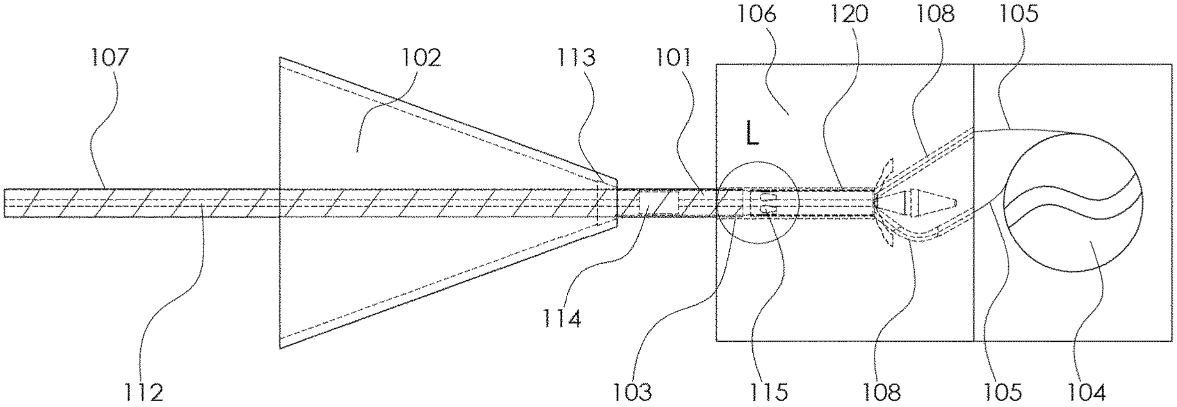
FIGS. 24 to 28 including details K to N: the figures show how the prosthesis is crimped into a peel-off tube (120) and how the peel-off tube is taken off according to the disclosure.
Figure 24:
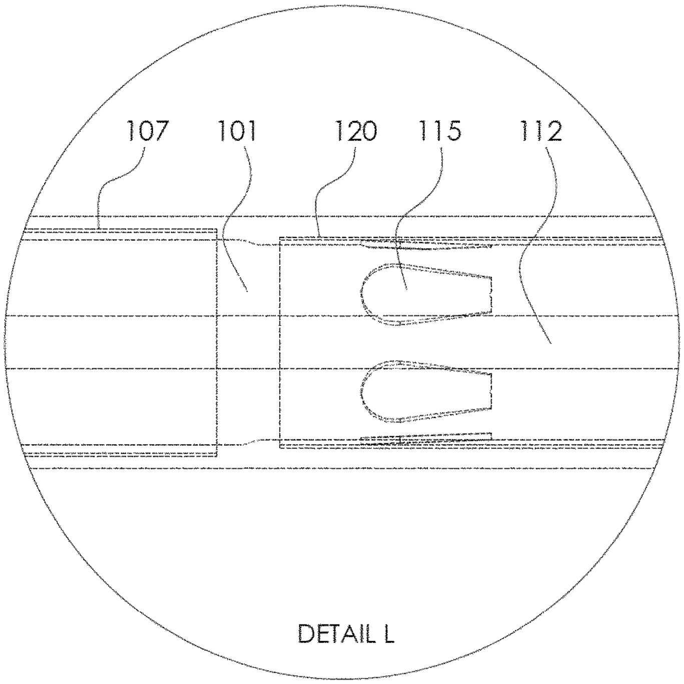

Accordingly, FIG. 24 shows how the prosthesis is crimped into a peel-off tube (120). The outer diameter of the peel-off tube is smaller than the inner diameter of the outer catheter shaft. Therefore the peel-off tube must be placed on the catheter during assembly, before the tip is bonded to the inner catheter shaft.

Figure 25:
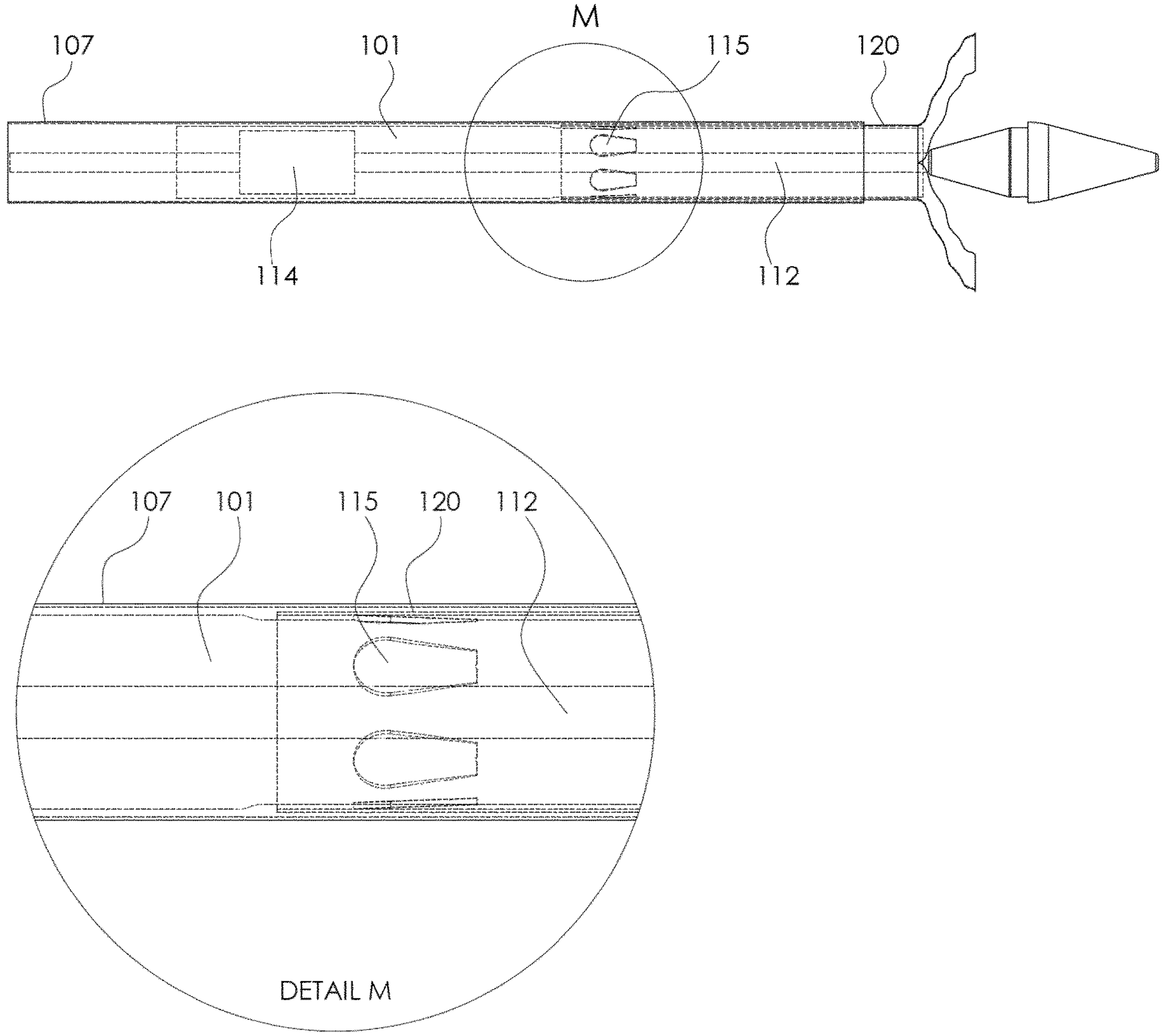

FIG. 25 describes the next step of the procedure according to the disclosure wherein the outer catheter shaft (107) is advanced over the peel-off tube (120), holding the prosthesis in a crimped state.

Figure 26:
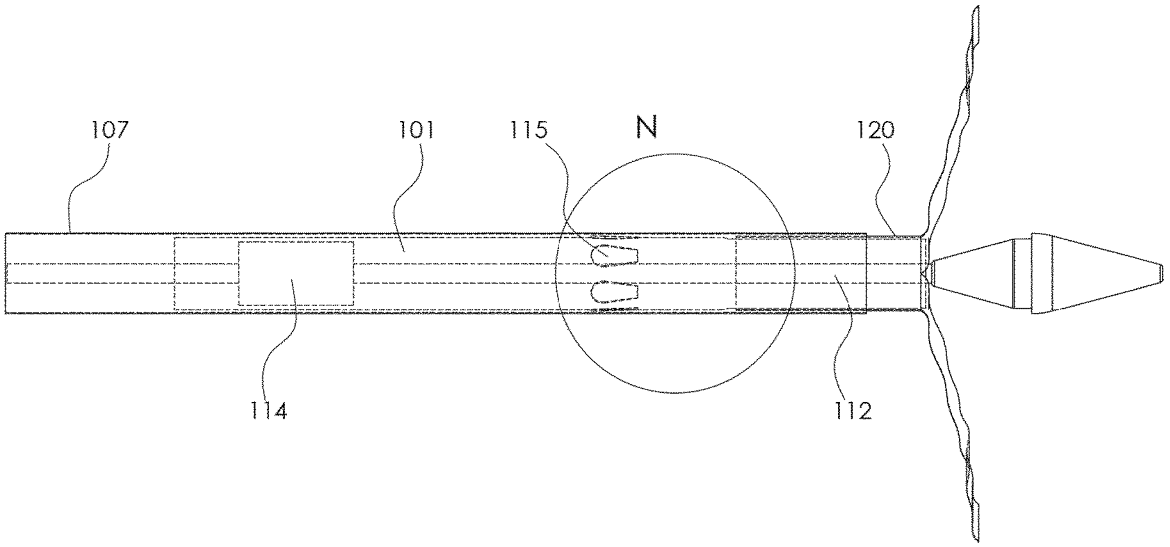
Figure 26:
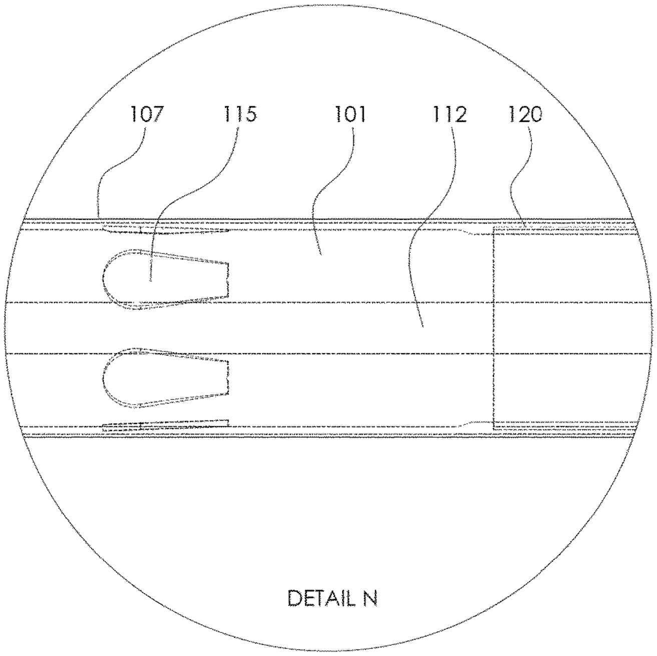

In FIG. 26 the peel-off tube is pulled out of the outer catheter shaft and peeled-off/split in half at the distal end of the catheter. This will allow the outwardly protruding features/anchoring features to expand slightly to the inner diameter of the outer catheter shaft.

Figure 27:
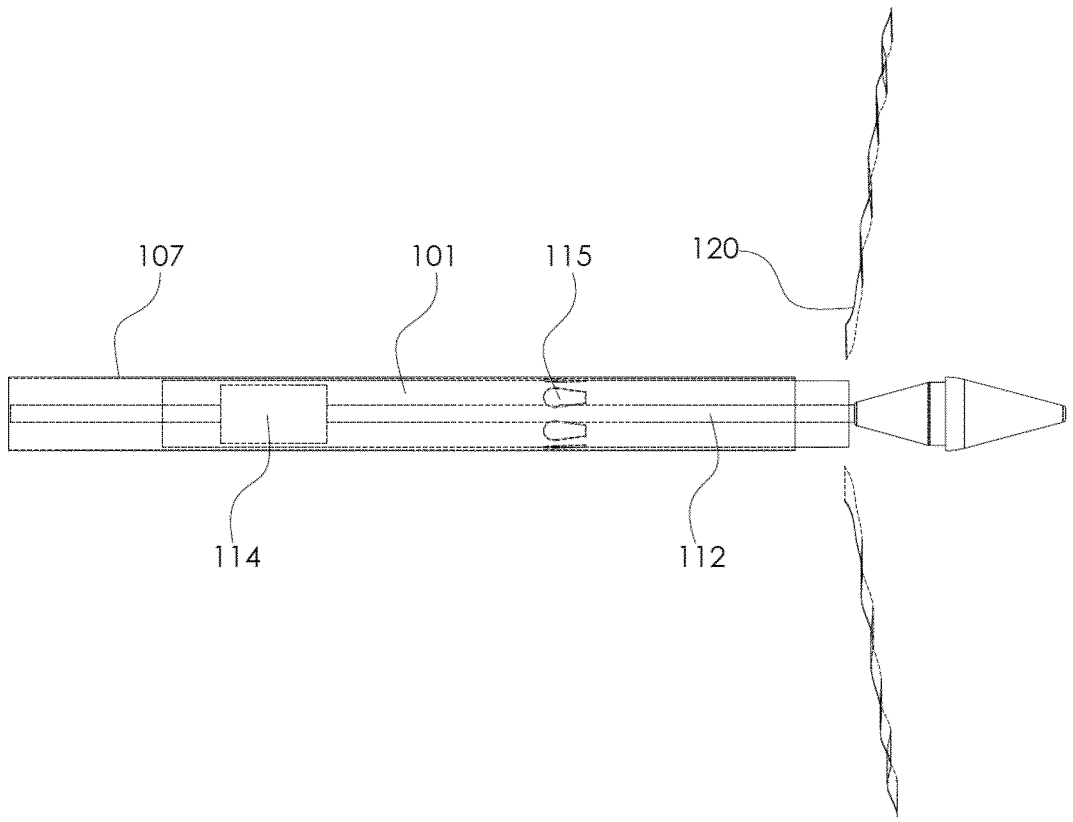

As is seen in FIG. 27 finally, the peel-off tube is removed completely and disposed.

Figure 28:
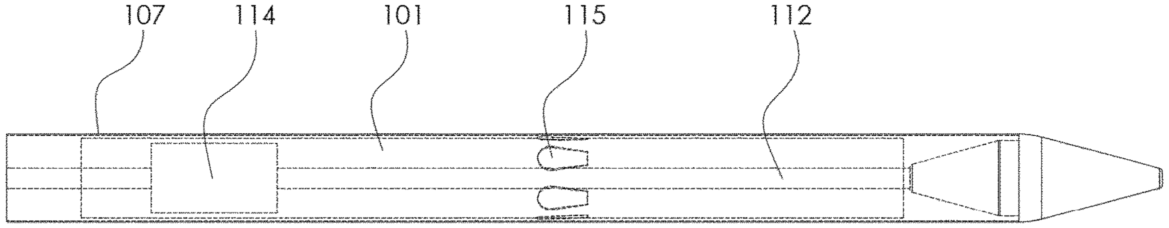

FIG. 28 shows how the outer catheter shaft is advanced a few more millimeters to close the system, upon which it is ready for use/implantation.

REFERENCE NUMBER LIST

101 Prosthesis
102 Funnel
103 Tubular structure (within base of loading system)
104 Rotatable wheel
105 Pulling suture
106 Base
107 Outer catheter shaft
108 Pulling suture guidance hole (within base of loading system)
109 Crimping suture
110 Suture guide
111 Suture access hole
112 Guide wire shaft with catheter tip
113 Flared telescoping tube
114 Stent holder
115 Additional/non-smooth stent feature/anchoring feature
116 Crimping suture for additional/non-smooth stent feature
117 Rotatable pin
118 Crimping tube for additional/non-smooth stent feature
119 Radial crimper
120 Peel-off tube

The invention claimed is:

1. An assembly of parts for crimping and/or loading a stent or stent-based prosthesis onto a delivery device or for converting a stent or stent-based prosthesis from an expanded diameter to a compressed diameter, comprising:

(a) a funnel;

(b) rotatable wheel;

(c) at least one pulling suture releasably attached or deconnectable to the stent or stent-based prosthesis;

(d) at least one pulling suture guidance hole for passing the at least one pulling suture through;

(e) a tubular structure having an opening in an axial direction within a base part, wherein the base part is free of a through-hole in the axial direction; and (f) a peel-off tube capable of holding a portion of the stent-based prosthesis in a crimped state, wherein an outer diameter of the peel-off tube is smaller than an inner diameter of an outer shaft of a catheter, wherein the peel-off tube is configured to be split longitudinally and separated from the stent or stent-based prosthesis by pulling during loading into the catheter;

wherein the stent or stent-based prosthesis comprises a non-smooth surface.

2. The assembly of parts of claim 1, wherein the at least one pulling suture comprises two pulling sutures, wherein the two pulling sutures are connected to the rotatable wheel.

3. The assembly of parts of claim 2, wherein the at least one pulling suture comprises loops or a slideable knot, and/or the at least one pulling suture is connected with a crimping suture, and/or the crimping suture is releasably attached to a prosthesis.

4. The assembly of parts of claim 1, wherein the funnel comprises at least two parts connected by a disengageable locking mechanism;

or wherein the assembly of parts further comprises the catheter releasably connected to the stent or stent-based prosthesis; or wherein the assembly of parts comprises two pulling sutures and two pulling suture guidance holes;

or wherein the assembly of parts further comprises the at least one pulling suture access hole; or wherein the assembly of parts further comprises a catheter tip mating cavity; or wherein the assembly of parts further comprises a flared telescoping tube; or wherein the assembly of parts further comprises the base part, wherein the base part comprises at least two parts which are releasably connected to the funnel.

5. The assembly of parts of claim 4, wherein the assembly of parts comprises a flared telescoping tube, wherein the flared telescoping tube is made out of polytetrafluoroethylene (PTFE).

6. The assembly of parts of claim 1, wherein:

the funnel and the base part are releasably connected; or the assembly of parts is releasably connected with the catheter.

7. A system comprising an assembly of parts according to claim 1, further comprising a prosthesis and a catheter.

8. The assembly of parts of claim 1, further comprising a crimping suture that is releasably or deconnectably attached to a prosthesis.

9. The assembly of parts of claim 1, wherein the at least one pulling suture comprises a tissue, a wire, a thread, or a filament, optionally a metal wire, thread, or filament.

10. The assembly of parts of claim 1, wherein the stent or stent-based prosthesis exhibits a step.

11. The assembly of parts of claim 1, wherein the assembly of parts includes a splitter device configured to split the peel-off tube.

12. An assembly of parts for crimping and/or loading a stent or stent-based prosthesis onto a delivery device or for converting a stent or stent-based prosthesis from an expanded diameter to a compressed diameter, comprising:

(a) a funnel;

(b) rotatable wheel;

(c) at least one pulling suture releasably attached or deconnectable to the stent or stent-based prosthesis;

(d) at least one pulling suture guidance hole for passing the at least one pulling suture through;

(e) a tubular structure within a base part;

(f) a peel-off tube capable of holding a portion of a stent or stent-based prosthesis in a crimped state, wherein an outer diameter of the peel-off tube is smaller than an inner diameter of an outer shaft of a catheter, wherein the peel-off tube is configured to be split longitudinally and separated from the stent or stent-based prosthesis by pulling during loading into the catheter; and (g) a splitter device configured to split the peel-off tube;

wherein the stent or stent-based prosthesis comprises a non-smooth surface.

* * * * *